US010543081B2

(12) United States Patent
Naor et al.

(10) Patent No.: US 10,543,081 B2
(45) Date of Patent: Jan. 28, 2020

(54) HEART VALVE PROSTHESIS

(71) Applicant: Mitrassist Medical Ltd., Caesarea (IL)

(72) Inventors: Gil Naor, Hofit (IL); Yiftah Neta, Gilon (IL); Avner Geva, Tel-Aviv (IL); Gideon Meyer-Brodnitz, Yokneam (IL)

(73) Assignee: Mitrassist Medical Ltd., Caesarea (IL)

( * ) Notice: Subject to any disclaimer, the term of this patent is extended or adjusted under 35 U.S.C. 154(b) by 0 days.

(21) Appl. No.: 15/527,332

(22) PCT Filed: Nov. 17, 2015

(86) PCT No.: PCT/IL2015/051109
§ 371 (c)(1),
(2) Date: May 17, 2017

(87) PCT Pub. No.: WO2016/079737
PCT Pub. Date: May 26, 2016

(65) Prior Publication Data
US 2017/0367822 A1 Dec. 28, 2017

Related U.S. Application Data

(60) Provisional application No. 62/080,619, filed on Nov. 17, 2014.

(51) Int. Cl.
*A61F 2/24* (2006.01)
(52) U.S. Cl.
CPC .......... *A61F 2/2418* (2013.01); *A61F 2/2457* (2013.01); *A61F 2220/0016* (2013.01);
(Continued)

(58) Field of Classification Search
CPC ....................................................... A61F 2/24
See application file for complete search history.

(56) References Cited

U.S. PATENT DOCUMENTS 8,579,964 B2    11/2013  Lane et al.
2008/0071361 A1  3/2008  Tuval et al.
(Continued)

FOREIGN PATENT DOCUMENTS

EP        2478868       7/2012
WO    WO 2016/079737    5/2016

OTHER PUBLICATIONS

Communication Relating to the Results of the Partial International Search dated Mar. 4, 2016 From the International Searching Authority Re. Application No. PCT/IL2015/051109.
(Continued)

*Primary Examiner* — Matthew W Schall

(57) ABSTRACT

A device for artificial cardiac valve support, the device including an upstream portion designed to expand to have at least one dimension wider than a native heart valve annulus, a downstream portion attached to the upstream portion, the downstream portion also designed to expand to have at least a portion with at least one dimension wider than a native heart valve annulus, and a plurality of artificial valve commissure posts. A method for producing a device for artificial cardiac valve support, the method including producing an upstream portion, producing a downstream portion, and attaching the upstream portion to the downstream portion, producing a frame for artificial cardiac valve support. Related apparatus and methods are also described.

18 Claims, 22 Drawing Sheets

(52) U.S. Cl.
CPC ......... *A61F 2230/0034* (2013.01); *A61F 2230/0078* (2013.01); *A61F 2250/0039* (2013.01)

(56) References Cited

U.S. PATENT DOCUMENTS

| | | |
|---|---|---|
| 2012/0053682 A1 | 3/2012 | Kovalsky et al. |
| 2012/0271398 A1 | 10/2012 | Essinger et al. |
| 2014/0155990 A1 | 6/2014 | Nyuli et al. |
| 2014/0277402 A1 | 9/2014 | Essinger et al. |
| 2018/0078361 A1 | 3/2018 | Naor et al. |

OTHER PUBLICATIONS

International Preliminary Report on Patentability dated Jun. 1, 2017 From the International Bureau of WIPO Re. Application No. PCT/IL2015/051105. (8 Pages).
International Search Report and the Written Opinion dated Feb. 19, 2016 From the International Searching Authority Re. Application No. PCT/IL2015/051105.

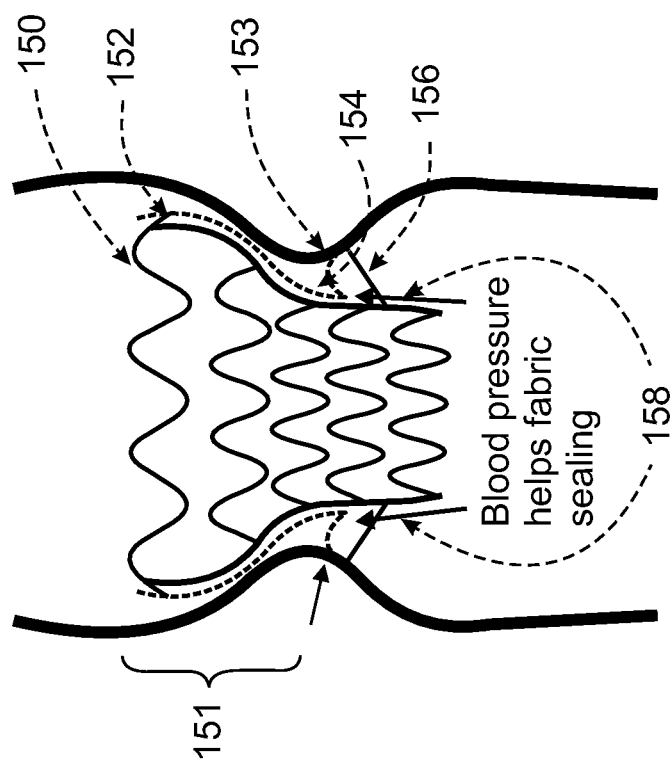
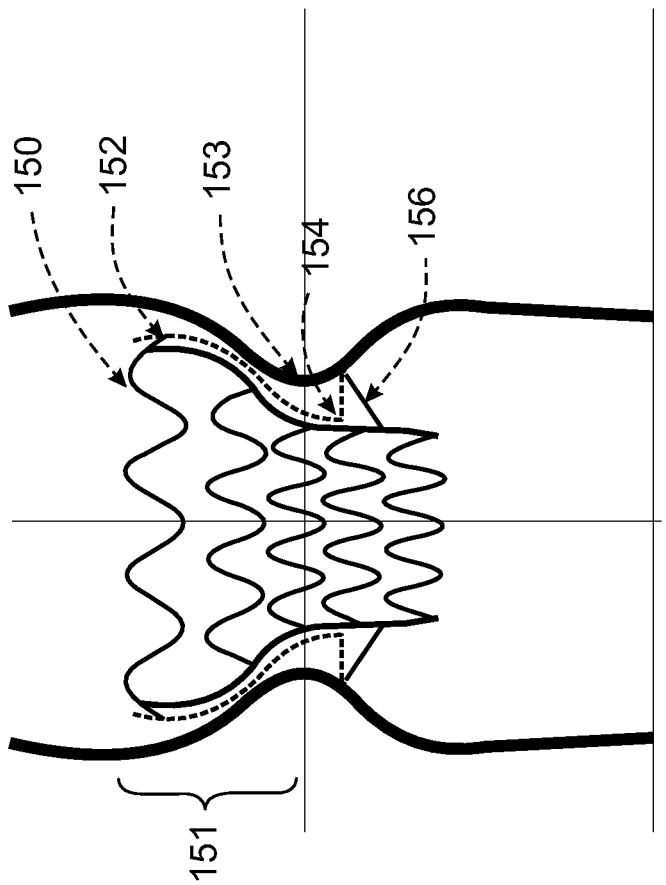

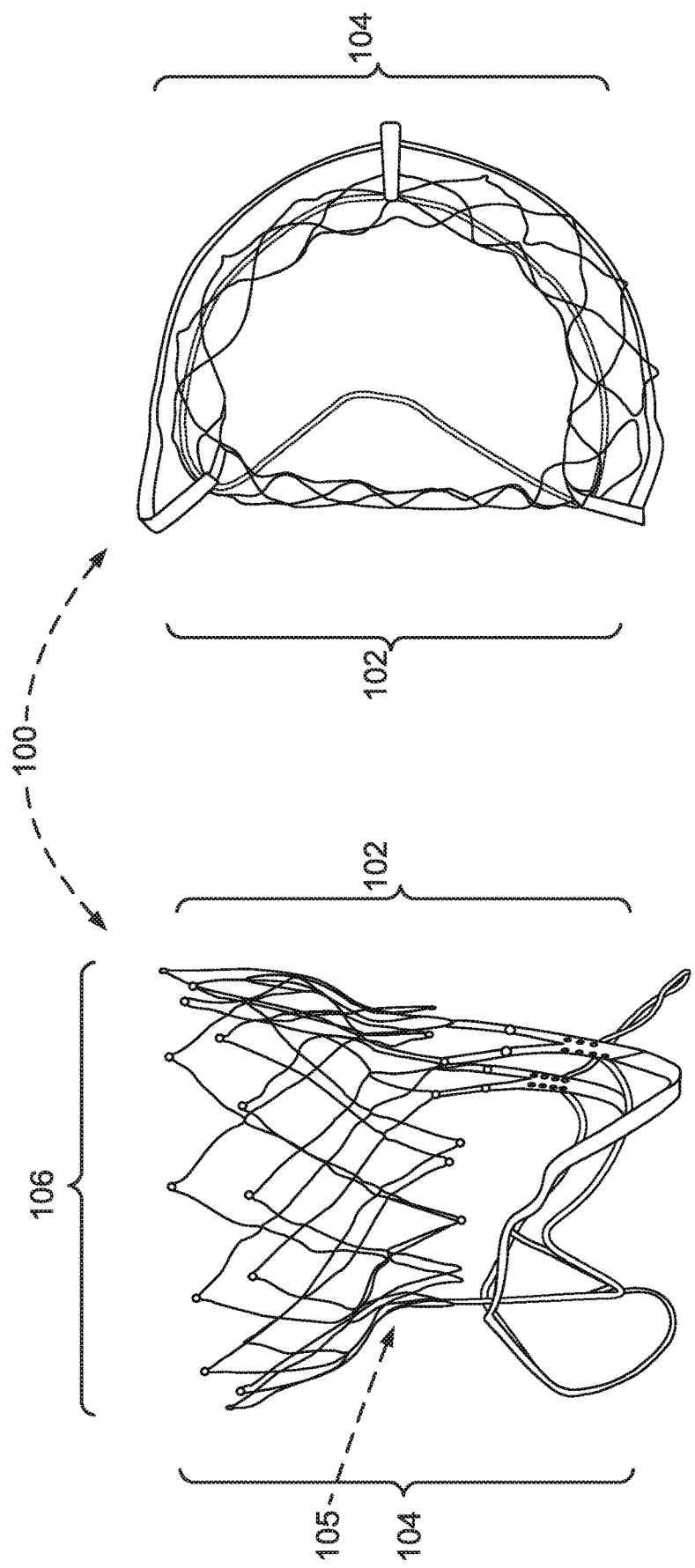

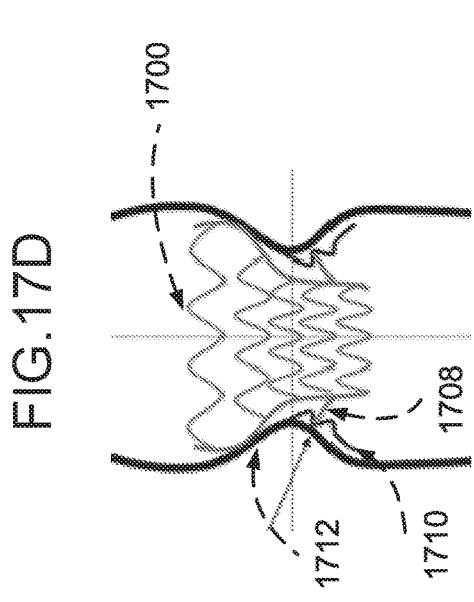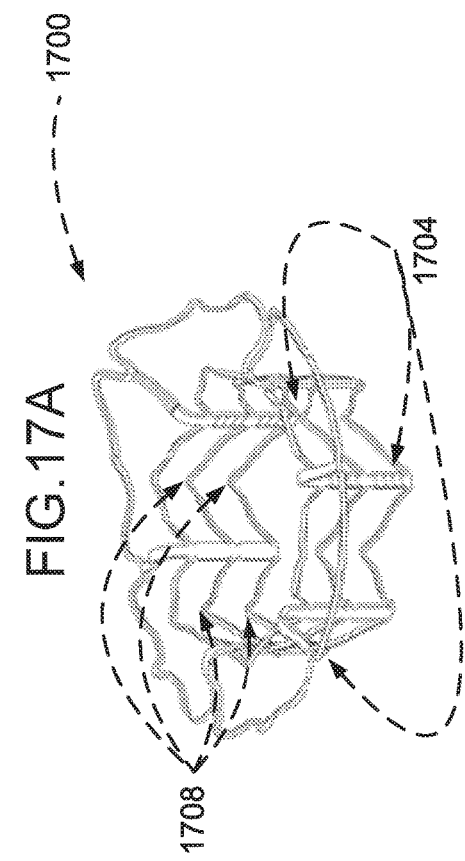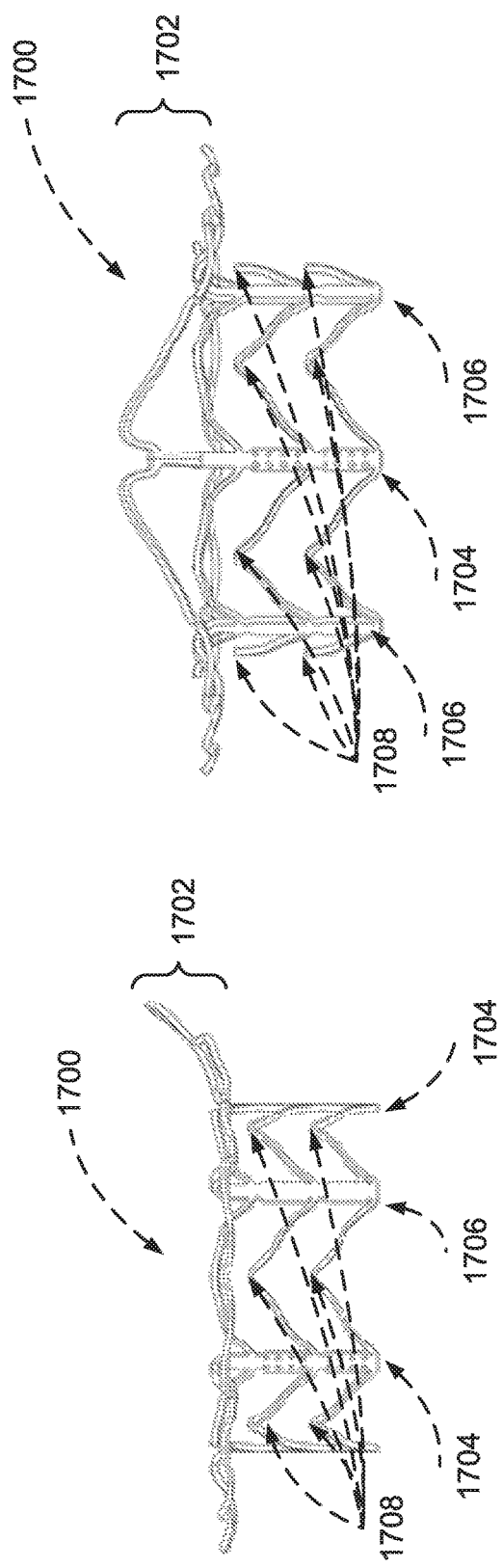
FIG.17D  FIG.17C  FIG.17A  FIG.17B

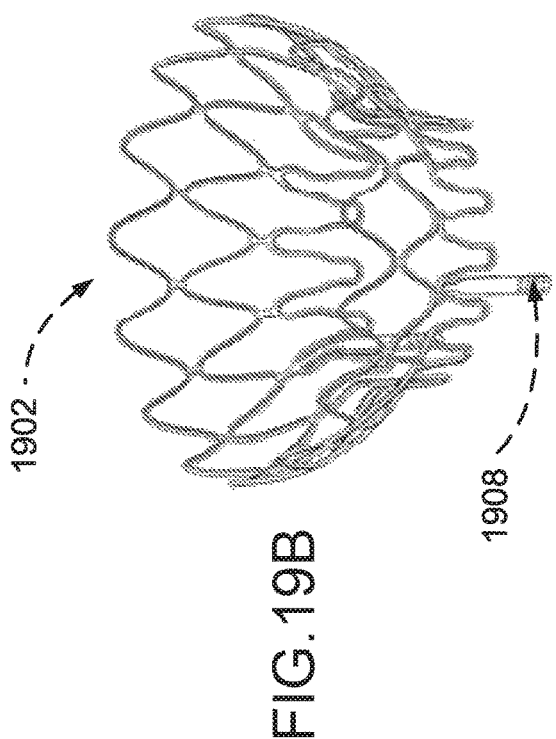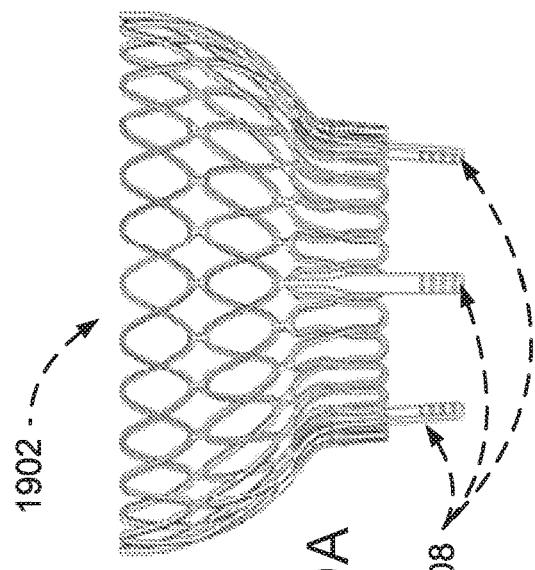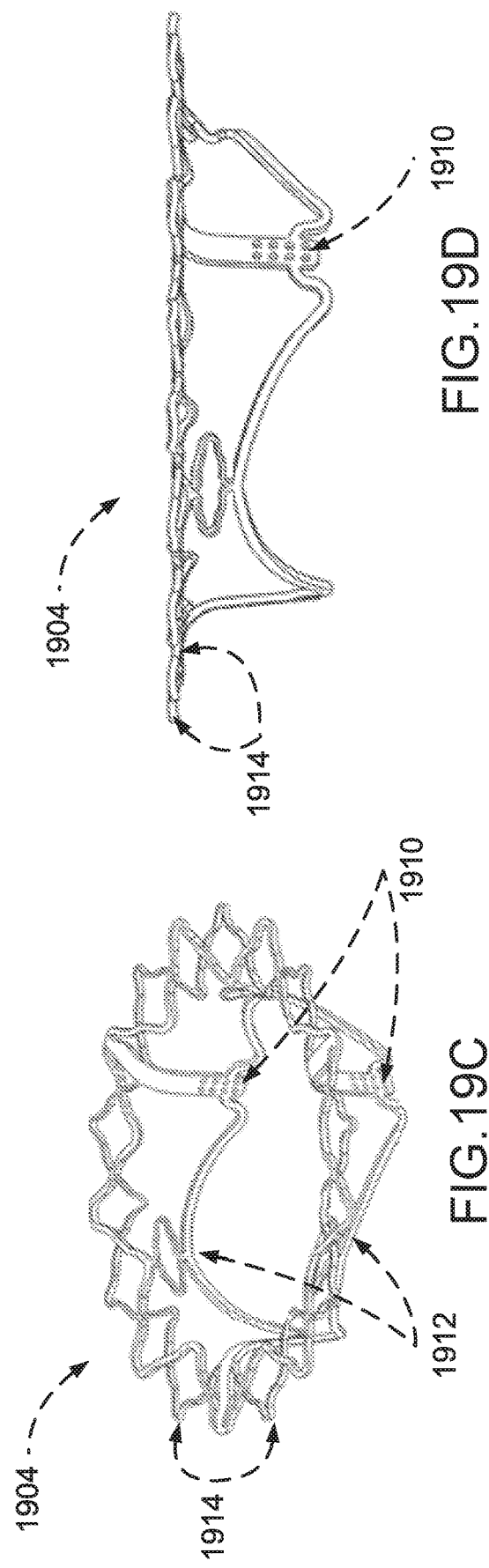

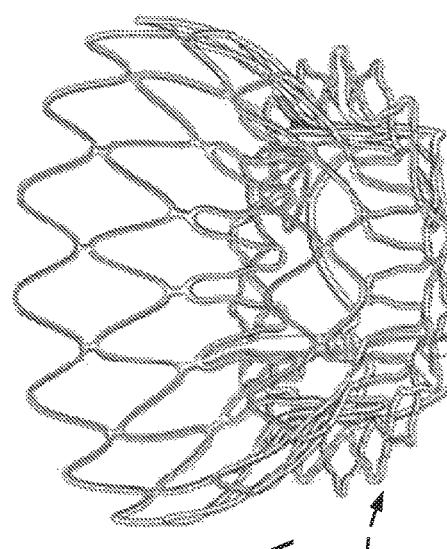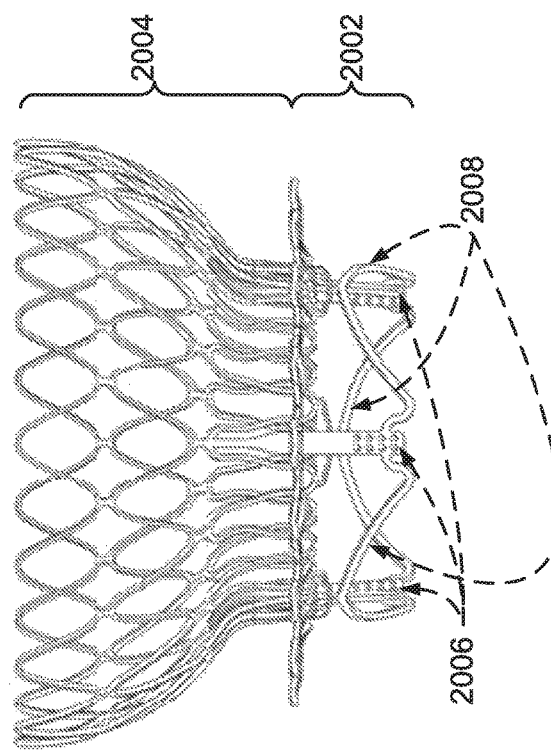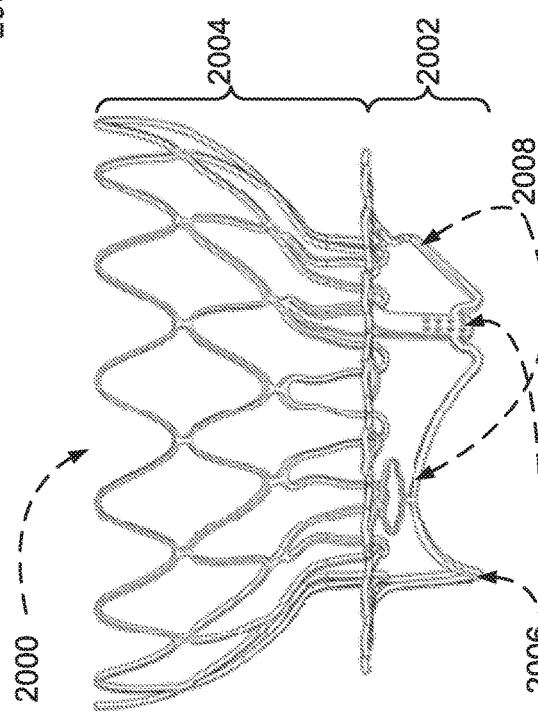

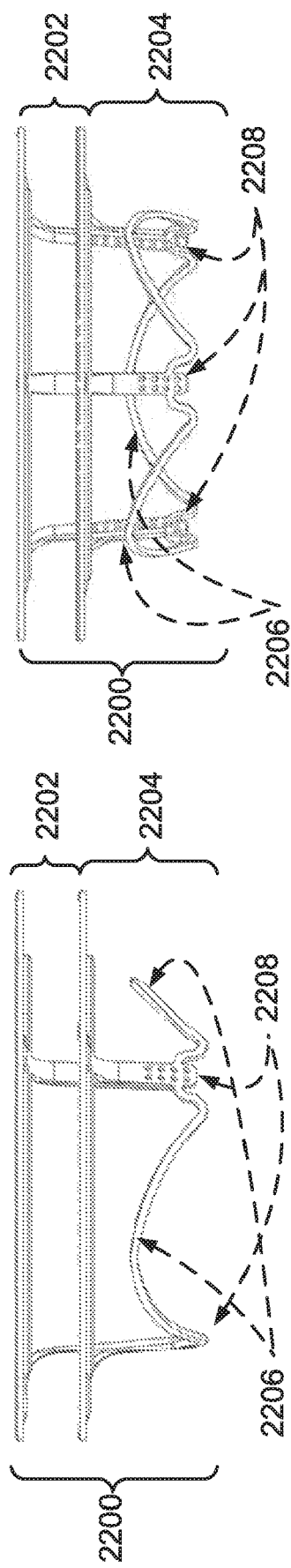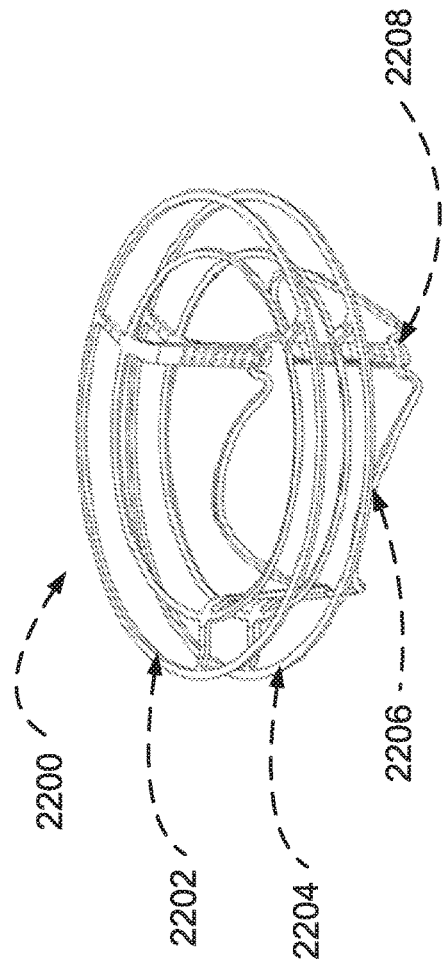
FIG.22A
FIG.22B
FIG.22C

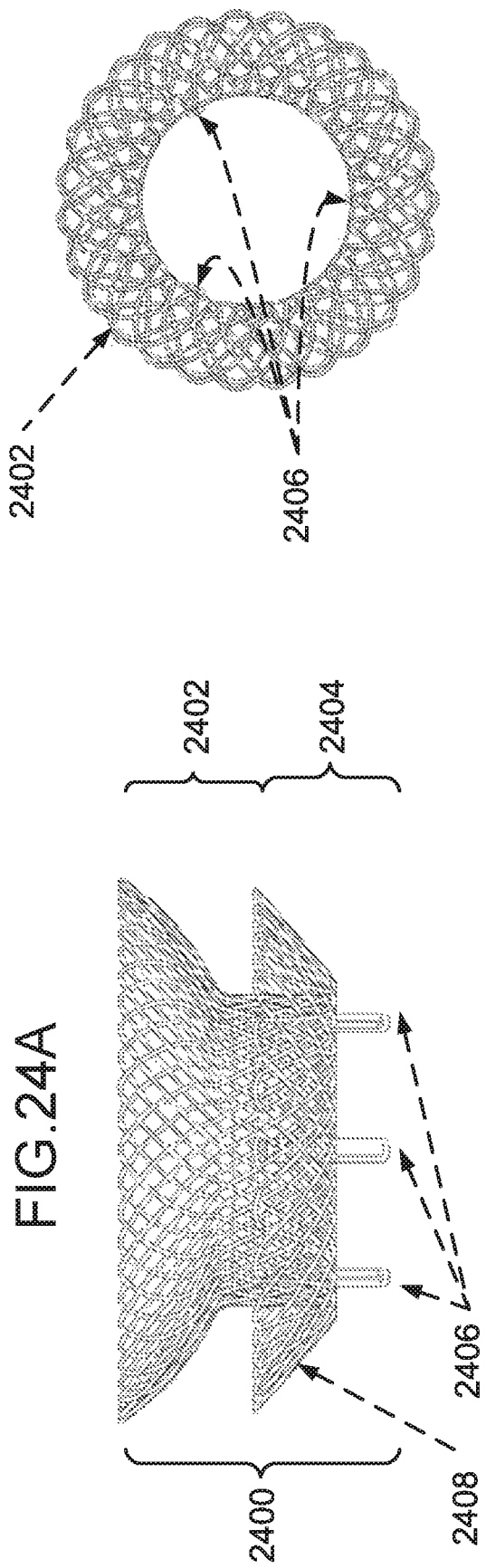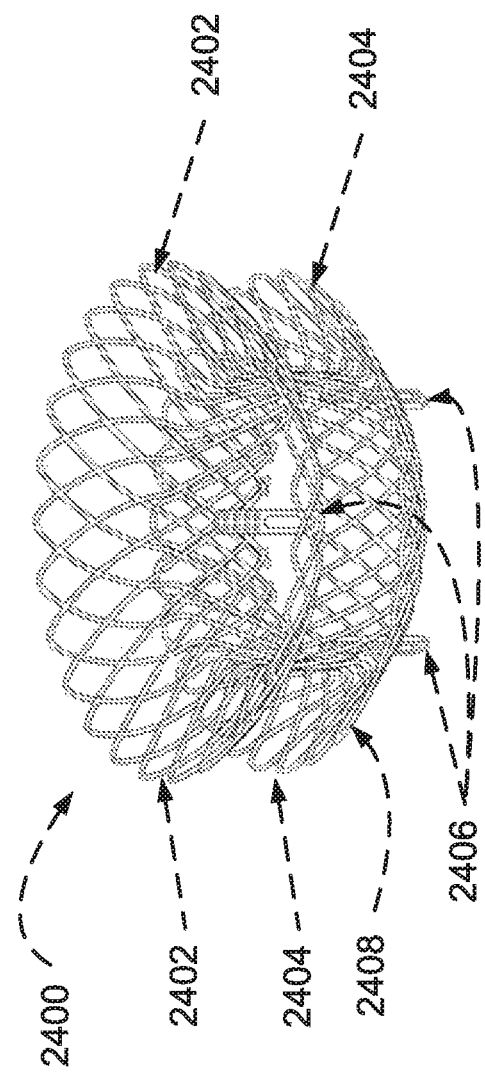

HEART VALVE PROSTHESIS

RELATED APPLICATIONS

This application is a National Phase of PCT Patent Application No. PCT/IL2015/051109 having International filing date of Nov. 17, 2015 which claims the benefit of priority under 35 USC § 119(e) of U.S. Provisional Patent Application No. 62/080,619 filed on Nov. 17, 2014. The contents of the above applications are all incorporated reference as if fully set forth herein in their entirety.

FIELD AND BACKGROUND OF THE INVENTION

The present invention, in some embodiments thereof, relates to a cardiac valve support, more particularly, but not exclusively, to a cardiac valve support for a prosthesis for a cardiac valve, and more particularly, but not exclusively, to a cardiac valve prosthesis.

The term "frame" is used throughout the present specification and claims to mean a support for a cardiac valve. In some embodiments the cardiac valve is optionally a fabric designed to act as a cardiac valve, attached to the frame. In some embodiments the cardiac valve is optionally a plastic and/or synthetic and/or metal valve.

The mitral valve and tricuspid valve are unidirectional heart valves which separate the left and right atria respectively, from corresponding heart ventricles. These valves have a distinct anatomical and physiological structure, having two (mitral) or three (tricuspid) sail-like leaflets connected to a sub-valvular mechanism of strings (chordae tendinae) and papillary muscles forming a part of the heart's ventricular shape, function and size.

The heart has four chambers: the right and left atria, and the right and left ventricles. The atria receive blood and then pump it into the ventricles, which then pump it out into the body.

Synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves which are supposed to ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

The opening and closing of heart valves occur primarily as a result of pressure differences. For example, the opening and closing of the mitral valve occurs as a result of the pressure differences between the left atrium and the left ventricle. During ventricular diastole, when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole, intra-ventricular pressure rises above the pressure in the atrium and pushes the mitral valve shut.

As noted above, these valves feature a plurality of leaflets connected to chordae tendinae and papillary muscles, which allow the leaflets to resist the high pressure developed during contractions (pumping) of the left and right ventricles. In a healthy heart, the chordae become taut, preventing the leaflets from being forced into the left or right atria and inverted. Prolapse is a term used to describe a condition wherein coaptation edges of each leaflet initially may coapt and close, but then the leaflets rise higher, the edges separate, and the valve leaks. This is normally prevented by a contraction of the papillary muscles and by the normal length of the chordae. Contraction of the papillary muscles is usually simultaneous with the contraction of the ventricle and serves to keep healthy valve leaflets tightly shut at peak contraction pressures exerted by the ventricle.

Valve malfunction can result from the chordae becoming stretched, and in some cases tearing. When a chord tears, the result is a flailed leaflet. Also, a normally structured valve may not function properly because of an enlargement of the valve annulus pulling the leaflets apart. This condition is referred to as a dilation of the annulus and generally results from heart muscle failure. In addition, the valve may be defective at birth or because of an acquired disease, usually infectious or inflammatory.

Diseases of the valves can cause either narrowing (stenosis) or dilatation (regurgitation, insufficiency) of the valve, or a combination of those. Surgical treatment for repair or replacement of the valves typically includes an open-heart procedure, extracorporeal circulation and, if replaced, a complete or partial resection of the diseased valve.

Additional background art includes:
U.S. Pat. No. 7,381,220 to Macoviak et al;
U.S. Pat. No. 8,579,964 to Lane et al;
US published patent application number 2014/0052237 of Lane et al;
US published patent application number 2010/0280606 of Naor;
US published patent application 2010/010017 of Letac et al;
US published patent application number 2007/0270943 of Solem et al;
US published patent application number 2007/0185571 of Kapadia et al;
US published patent application number 2007/0156233 of Kapadia et al;
US published patent application number 2006/0058871 of Zakay et al;
US Published Patent Application 2004/0127981A1 of Randert et al;
US published patent application number 2003/0199975 of Gabbay;
PCT patent application number IL2014/050414 of Naor;
PCT published patent application WO2013/076724 of Vaturi;
PCT published patent application WO2011/137531 of Lane et al;
PCT published patent application number WO 2011/069048 of Chau et al;
PCT published patent application number WO 2011/106544 of Tuval et al;
PCT published patent application number WO 2011/137531 of Lane et al;
PCT Published Patent Application WO2010/106438 of Naor et al; and
PCT published patent application number WO 2005/027797 of Ersin.
PCT published patent application number WO 2004/089250 of Realyvasquez et al.

PCT published patent application number WO 2004/030568 of Macoviak et al.

The disclosures of all references mentioned above and throughout the present specification, as well as the disclosures of all references mentioned in those references, are hereby incorporated herein by reference.

SUMMARY OF THE INVENTION

The present invention, in some embodiments thereof, relates to a cardiac valve support, more particularly, but not exclusively, to a cardiac valve support for a prosthesis for a mitral valve.

The present invention, in some embodiments thereof, also relates to a prosthesis for a heart valve.

In some embodiments, the cardiac valve support is placed over a subject's natural heart valve and is designed to anchor itself in place.

In some embodiments, the prosthetic valve may be a valve as described in above-mentioned US published patent application number 2010/0280606 of Naor or in above-mentioned PCT patent application number IL2014/050414 of Naor.

According to an aspect of some embodiments of the present invention there is provided a device for artificial mitral valve support including an expandable frame configured so at least part of the frame can expand larger than a natural mitral valve annulus, to prevent the frame from shifting downstream of the natural mitral valve annulus, a pair of commissure posts attached at one end to the frame, the commissure posts configured to extend downstream of the mitral valve annulus through the commissures of the natural mitral valve, a posterior extension attached at a first end to the frame, the posterior extension configured to extend downstream of the mitral valve annulus and partway back and out, pushing a posterior leaflet of the natural mitral valve toward a ventricle wall, and a supporting arch attaching a downstream end of a first one of the commissure posts to a downstream end of the posterior extension to a downstream end of a second one of the commissure posts.

According to some embodiments of the invention, the supporting arch includes a bend for accommodating papillary muscles.

According to some embodiments of the invention, further including a pair of anterior leaflet hooks, each one of the pair of anterior leaflets hooks configured to engage chordae attached to the anterior leaflet and pull the anterior leaflet in opposing directions.

According to some embodiments of the invention, further including a plurality of anterior leaflet grabbers, each one of the plurality of anterior leaflet grabbers including one end attached to the frame and one end configured to grasp the anterior leaflet of the natural mitral valve.

According to some embodiments of the invention, further including a pair of trigon anchors, each one of the pair of trigon anchors including one end attached to the frame and one end configured to push against a cardiac valve trigon.

According to some embodiments of the invention, the supporting arch is configured to be between 2 and 20 millimeters below an annular plane of the natural mitral valve when placed in a natural mitral valve.

According to some embodiments of the invention, the supporting arch is covered by a sheet of flexible material.

According to some embodiments of the invention, the frame includes a D-shaped section of the frame configured to be placed at the natural mitral valve annulus and push the natural mitral valve annulus into a shape of the D-shaped section.

According to some embodiments of the invention, the supporting arch is configured to be between 5 and 20 millimeters larger in diameter than the D-shaped section of the frame. According to some embodiments of the invention, the supporting arch is configured to be between 2 and 20 millimeters distant from an upstream edge of the D-shaped section of the frame.

According to some embodiments of the invention, the D-shaped section includes a lumen having lumen walls parallel to an axis of a natural mitral valve annulus.

According to some embodiments of the invention, the lumen walls of the D-shaped section are in a range between 5 millimeters and 15 millimeters long.

According to some embodiments of the invention, further including a commissure arch attaching a downstream end of a first one of the commissure posts to a downstream end of a second one of the commissure posts.

According to an aspect of some embodiments of the present invention there is provided a method of supporting an artificial mitral valve including providing a frame for anchoring the artificial mitral valve, configured to be placed upstream of a natural mitral valve annulus and shaped to be able to expand to a diameter larger than the natural mitral valve annulus, to prevent the frame from shifting downstream of the natural mitral valve annulus, the frame further including a pair of commissure posts attached at one end to the frame, the commissure posts configured to extend downstream of a mitral valve annulus through the commissures of the natural mitral valve, a posterior extension attached at a first end to the frame, the posterior extension configured to extend downstream of the mitral valve annulus and partway back and out, pushing a posterior leaflet of the natural mitral valve toward a ventricle wall, and a supporting arch attaching a downstream end of a first one of the commissure posts to a downstream end of the posterior extension to a downstream end of a second one of the commissure posts, placing at least part of the frame in a left cardiac atrium, passing the posterior extension and the supporting arch through the natural mitral valve commissures so as to push against the posterior leaflet of the natural mitral valve toward a ventricle wall, and locating the commissure posts at the natural mitral valve commissures.

According to some embodiments of the invention, the frame further includes a pair of hooks, and further including using each one of the pair of hooks to engage chordae attached to an anterior leaflet.

According to some embodiments of the invention, the frame further includes anterior leaf grabbers, the anterior leaf grabbers including a plurality of extensions, each one of the plurality of extensions including one end attached to the frame and one end configured to grasp an anterior leaflet of the natural mitral valve, and further including using the anterior leaf grabbers to grasp the natural anterior mitral valve leaflet.

According to some embodiments of the invention, the frame includes a D-shaped section of the frame configured to be placed at the natural mitral valve annulus and push the natural mitral valve annulus into a shape of the D-shaped section, and further including placing the D-shaped section of the frame at the natural mitral valve annulus.

According to an aspect of some embodiments of the present invention there is provided a device for artificial mitral valve support including an expandable frame configured so at least part of the frame can expand larger than a natural mitral valve annulus, to prevent the frame from shifting downstream of the natural mitral valve annulus, a pair of commissure posts attached at one end to the frame, the commissure posts configured to extend downstream of the mitral valve annulus through the commissures of the natural mitral valve, and anterior leaflet grabbers, the anterior leaflet grabbers including a plurality of extensions, each one of plurality of extensions including one end attached to the frame and one end configured to grasp an anterior leaflet of the natural mitral valve.

According to some embodiments of the invention, further including a pair of hooks, each one of the pair of hooks configured to engage chordae attached to the anterior leaflet and pull the anterior leaflet in opposing directions.

According to some embodiments of the invention, further including a posterior extension attached at a first end to the frame, the posterior extension configured to extend downstream of the mitral valve annulus and partway back and out, pushing a posterior leaflet of the natural mitral valve toward a ventricle wall, and a supporting arch attaching a downstream end of a first one of the commissure posts to a downstream end of the posterior extension to a downstream end of a second one of the commissure posts.

According to an aspect of some embodiments of the present invention there is provided a method of supporting an artificial mitral valve including providing a frame for anchoring the artificial mitral valve, configured to be placed upstream of a natural mitral valve annulus and shaped to expand larger than the natural mitral valve annulus to prevent the frame from shifting downstream of the natural mitral valve annulus, the frame further including a plurality of anterior leaflet grabbers, each one of the plurality of anterior leaflet grabbers including one end attached to the frame and one end configured to grasp an anterior leaflet of the natural mitral valve, and further including using the anterior leaf grabbers to grasp the natural anterior mitral valve leaflet.

According to some embodiments of the invention, the frame further includes a pair of hooks, and further including using each one of the pair of hooks to engage chordae attached to the natural anterior mitral valve leaflet.

According to some embodiments of the invention, the frame further includes a pair of commissure posts attached at one end to the frame, the commissure posts configured to extend downstream of the mitral valve annulus through the commissures of the natural mitral valve, a posterior extension attached at a first end to the frame, the posterior extension configured to extend downstream of the mitral valve annulus and partway back and out, pushing a posterior leaflet of the natural mitral valve toward a ventricle wall, and a supporting arch attaching a downstream end of a first one of the commissure posts to a downstream end of the posterior extension to a downstream end of a second one of the commissure posts, and further including passing the posterior extension and the supporting arch through the natural mitral valve commissures so as to push against the posterior leaflet of the natural mitral valve toward a ventricle wall, and locating the commissure posts at the natural mitral valve commissures.

According to some embodiments of the invention, the frame includes a D-shaped section of the frame configured to be placed at the natural mitral valve annulus and push the natural mitral valve annulus into a shape of the D-shaped section, and further including placing the D-shaped section of the frame at the natural mitral valve annulus.

According to an aspect of some embodiments of the present invention there is provided a device for artificial cardiac valve support, the device including an upstream portion designed to expand to have at least one dimension wider than a native heart valve annulus, a downstream portion attached to the upstream portion, the downstream portion also designed to expand to have at least a portion with at least one dimension wider than a native heart valve annulus, and a plurality of artificial valve commissure posts.

According to some embodiments of the invention, the upstream portion and the downstream portion include separate components designed to be attached to each other.

According to some embodiments of the invention, the upstream portion is produced from material selected from a group consisting of a tube, a sheet, and braided wire.

According to some embodiments of the invention, the downstream portion is produced from material selected from a group consisting of a tube, a sheet, and braided wire.

According to some embodiments of the invention, the commissure posts are attached to the downstream portion.

According to some embodiments of the invention, the commissure posts are attached to the upstream portion.

According to some embodiments of the invention, the downstream portion includes an expandable mesh designed to expand to a diameter greater than the diameter of the native heart valve annulus.

According to some embodiments of the invention, the downstream portion includes a single ring with a diameter greater than the diameter of the native heart valve annulus.

According to some embodiments of the invention, the downstream portion includes a single asymmetrically shaped ring with at least one dimension greater than a diameter of the native heart valve annulus.

According to some embodiments of the invention, the downstream portion further includes support arcs connecting the commissure posts.

According to some embodiments of the invention, the support arcs are designed to expand against native heart leaflets.

According to some embodiments of the invention, the support arcs are designed to expand such that the downstream portion has a diameter great than the diameter of the native heart valve annulus.

According to some embodiments of the invention, the commissure posts include holes for suturing a flexible sheet.

According to some embodiments of the invention, the plurality of commissure posts consists of three commissure posts.

According to some embodiments of the invention, the commissure posts extend downstream, then bend outward and are attached to a balcony having a diameter, at least in one direction, greater than a width of the native heart valve annulus.

According to some embodiments of the invention, further including support posts between the commissure posts.

According to some embodiments of the invention, the support posts extend downstream, then bend outward and are attached to a balcony having a diameter, at least in one direction, greater than a width of the native heart valve annulus.

According to some embodiments of the invention, the upstream portion includes an expandable mesh designed to expand to a diameter great than the diameter of the native heart valve annulus.

According to some embodiments of the invention, the upstream portion includes a single ring with designed to expand to a diameter great than the diameter of the native heart valve annulus.

According to some embodiments of the invention, the upstream portion includes a single asymmetrically shaped ring with at least one dimension greater than a diameter of the native heart valve annulus.

According to some embodiments of the invention, further including a flexible sheet attached to the commissure posts and designed to act as an artificial cardiac valve allowing blood flow from an upstream side to a downstream side of the device and block blood flow from the downstream side to the upstream side of the device.

According to some embodiments of the invention, the flexible sheet includes several flexible sheets designed and attached to each other to form the artificial cardiac valve.

According to some embodiments of the invention, the flexible sheet includes a woven fabric. According to some embodiments of the invention, the flexible sheet includes a biocompatible synthetic sheet. According to some embodiments of the invention, the flexible sheet includes a pericardium tissue sheet.

According to some embodiments of the invention, the flexible sheet is attached to the device and is designed to be free to inflate up to contacting walls of a native heart.

According to an aspect of some embodiments of the present invention there is provided a method for producing a device for artificial cardiac valve support, the method including producing an upstream portion, producing a downstream portion, and attaching the upstream portion to the downstream portion, producing a frame for artificial cardiac valve support.

According to some embodiments of the invention, further including suturing a flexible sheet to the frame, producing an artificial cardiac valve sutured to the frame.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

FIGS. 1B and 1C are simplified illustrations of an example embodiment of the invention;

FIGS. 1D and 1E are top view and side view images respectively, depicting an example embodiment of the invention;

FIGS. 17A, 17B and 17C are simplified illustrations of a cardiac valve support according to an example embodiment of the invention;

FIG. 17D is a cross-sectional side view of the cardiac valve support in location in a natural cardiac valve;

FIGS. 19A, 19B, 19C and 19D are simplified illustrations of a cardiac valve support according to an example embodiment of the invention;

FIGS. 20A, 20B and 20C are simplified illustrations of a cardiac valve support according to an example embodiment of the invention;

FIGS. 22A, 22B and 22C are simplified illustrations of a cardiac valve support according to an example embodiment of the invention;

FIGS. 24A, 24B and 24C are simplified illustrations of a cardiac valve support according to an example embodiment of the invention.

DESCRIPTION OF SPECIFIC EMBODIMENTS OF THE INVENTION

Figure 1A:
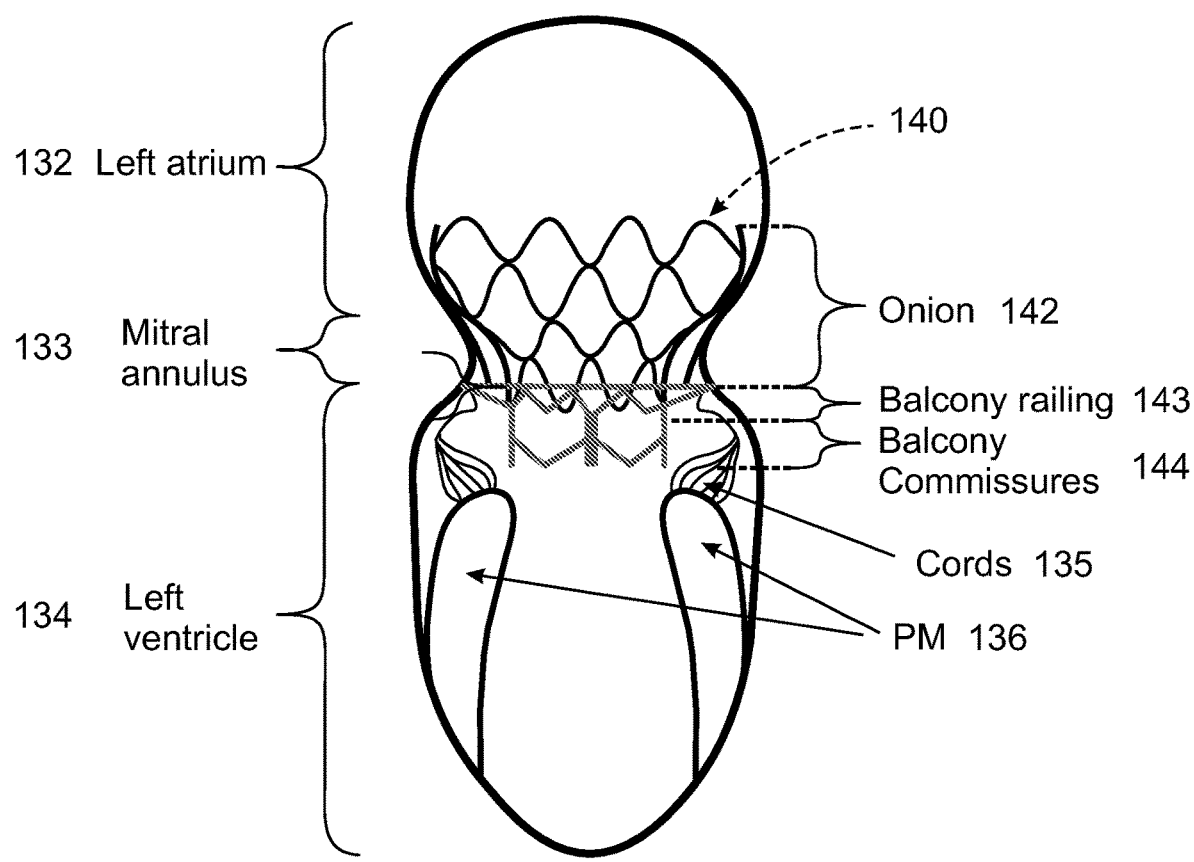
FIG. 1A is a simplified illustration of an example embodiment of the invention.

The present invention, in some embodiments thereof, relates to a cardiac valve support, more particularly, but not exclusively, to a cardiac valve support for n prosthesis for a cardiac valve.

The present invention, in some embodiments thereof, also relates to the prosthesis for a cardiac valve.

In some embodiments, the cardiac valve support is placed over a subject's natural heart valve. The subject's natural heart valve may be defective, allowing some blood to leak back through the natural heart valve during a natural heart beat cycle.

An aspect of some embodiments includes an expandable stent-like frame which potentially prevents the cardiac valve support from shifting downstream from an atrium into a ventricle of the heart and/or from the ventricle to the atrium.

In some embodiments, a stent-like, cage-like, frame section is provided, designed to optionally expand wider than an cardiac valve annulus, so as to prevent the frame from shifting downstream of the annulus.

An aspect of some embodiments includes a D-shaped section shaped similarly to a healthy natural cardiac valve annulus. In some embodiments the D-shaped section of the frame is designed to be placed at the cardiac valve annulus, and optionally to expand against sides of the annulus. In some embodiments the D-shaped section is shaped so as to reshape the natural mitral valve to a pre-diseased shape. In some embodiments the D-shaped section is shaped so as to press against all sides of the natural valve annulus and block potential blood leaking back from the ventricle to the atrium.

An aspect of some embodiments includes an expandable frame made from two portions—an upstream portion and a downstream portion. In some embodiments the upstream portion and the downstream portion are manufactured separately, and subsequently attached to each other. Such embodiments enable a physician to pick a first specific design and/or size of an upstream portion, and to pick a specific design and/or size, possibly different from the first pick, and decide to have them attached to each other to produce a frame.

An aspect of some embodiments include a downstream portion which includes a section designed to expand to be wider, at least in one dimension, than an annulus of a cardiac valve, to prevent the cardiac valve support from shifting upstream under blood pressure. The section which is designed to be wider is optionally made of a wire extending around the downstream portion; and/or a flexible metal sheet cut to form a wider section when expanded; and/or braided wire; and/or wire in form of arcs whose tips are designed to push against walls of the heart.

An aspect of some embodiments include an upstream portion which includes a section designed to expand to be wider, at least in one dimension, than an annulus of a cardiac valve, to prevent the cardiac valve support from shifting downstream under blood pressure. The section which is designed to be wider is optionally made of a wire extending around the upstream portion; and/or a flexible metal sheet cut to form a wider section when expanded; and/or braided wire; and/or wire in form of arcs.

An aspect of some embodiments includes commissure posts attached at an upstream end to the frame and located so as to extend downstream through the natural heart valve commissures. In some embodiments which include the commissure posts, a strut is provided connecting downstream ends of the commissure posts, potentially further strengthening the valve support shape and location within the natural heart valve.

An aspect of some embodiments includes a frame extension extending below the natural valve annulus and pushing a leaflet against the ventricle walls. The frame extension potentially anchors the cardiac valve support against shifting back upstream from a ventricle into an atrium of the heart.

In some embodiments, the frame extension is attached at a first end to the frame, and shaped to extend downstream of a cardiac valve annulus. In some embodiments which includes the commissure posts and the frame extension, a support arch is also provided, connecting downstream ends of the frame extension to downstream ends of the commissure posts, potentially further strengthening the valve support shape and location within the natural heart valve, and/or potentially spreading a back-pressure exerted on the valve support along the length of the support arch.

In some embodiments of the above, the cardiac valve support may be covered with such a material as to prevent blood from entering the atrium from the ventricle.

Various forms of the terms "native valve" and "native valve annulus" are meant to mean herein the valve or valve annulus already present in a subject, as opposed to an artificial valve or artificial valve annulus.

In some embodiments, the cardiac valve support is placed in a subject's heart valve without suturing the prosthesis to the heart.

In some embodiments, the cardiac valve support is placed in a subject's heart valve and the cardiac valve support is sutured to the heart.

In some embodiments, the cardiac valve support is sutured to the heart using less individual stitches than a typical cardiac valve support would require, since the cardiac valve support includes various anchoring extensions as described herein, and forces acting on the artificial valve are potentially smaller.

In some embodiments one or more flexible sheets are attached to the frame to form an artificial cardiac valve.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Reference is now made to FIG. 1A, which is a simplified illustration of an example embodiment of the invention.

FIG. 1A depicts a simplified illustration of an example embodiment of a cardiac valve support 140 for a prosthesis for a cardiac valve. Three portions of a natural heart are depicted, so as to illustrate these portions, which will be referred to many times in the course of the present specification.

An upstream portion 132 is depicted, the term upstream being used in relation to a direction of blood flow. By way of a non-limiting example the upstream portion is a left atrium. An annulus portion 133 is also depicted. A downstream portion 134 is also depicted—by way of a non-limiting example the downstream portion 134 is a left ventricle.

The example embodiment of a cardiac valve support 140 is depicted as including two general portions:

an upstream portion 142, also termed an onion, which is made to have at least some dimensions wider than the annulus portion 133 of the natural heart, preventing the cardiac valve support 140 from shifting downstream; and a downstream portion, also termed a balcony, which is made to have at least some dimensions wider than the annulus portion 133 of the natural heart, preventing the cardiac valve support 140 from shifting upstream.

The downstream portion of the example embodiment of FIG. 1A includes two portions—a balcony railing 143, which is made to have at least some dimensions wider than the annulus portion 133 of the natural heart, preventing the downstream portion from shifting downstream, and balcony commissures 144, which are made to provide support for a prosthetic cardiac valve.

In some embodiments the cardiac valve support 140 is constructed as a combination of three components: an onion component, such as the an upstream portion 142; several commissures-in-a-cage such as the balcony commissures 144 which optionally act as a skeleton of a prosthetic cardiac valve; and a balcony such as the balcony railing 143 for anchoring and optionally sealing between the cardiac valve support 140 and walls and/or annulus of the natural cardiac valve, below the native annulus. In some embodiments the commissures-in-a-cage include at least three commissures-in-a-cage, or six, commissures-in-a-cage, or nine commissures-in-a-cage, or more.

It is noted that from many embodiments will be described herein as having three commissure posts, and the embodiments are to be understood as having an integer number of commissure posts such as two, three, four, five, six, seven, eight, nine, ten and higher integer numbers.

In some embodiments the commissure posts serve for attaching artificial leaflets which act as artificial valves. In such embodiments, two commissure posts optionally serve for attaching two leaflets in a two-leaflet artificial valve; three commissure posts optionally serve for attaching three leaflets in a three-leaflet artificial valve, and so on.

In some embodiments the onion component, when expanded, is larger in diameter, or at least in one dimension, than the native annulus, and prevents the cardiac valve support 140 from shifting downstream of the natural mitral valve annulus.

In some embodiments, the onion component dimensions are larger than an annulus by at least, approximately, 10 mm. By way of a non-limiting example, for an annulus size of 30 mm, the onion component includes an expanded dimension of at least 40 mm. A maximal size of the onion component is typically less than an atrium diameter. Typical atrium sizes vary from 20-80 mm, depending on factors such as regurgitation, blood pressure and illness. In some embodiments an expanded dimension of the onion components may be in a range of 35 to 60, and even in a range of 20 to 90 mm. In some embodiment the onion dimension may be a diameter of a circle, and in some embodiments, for example when the onion component and/or the cardiac valve support has a D-shaped cross-section, the onion dimension may be the large dimension of the D-shape.

In some embodiments the onion is optionally made in a form of an expandable mesh, stent-like, and/or in a form of expandable petals.

In some embodiments the onion is optionally produced from a metal tube cut to a specific expandable shape, a metal sheet cut to a specific expandable shape, and/or a metal wire, and given a shape of an onion as described herein.

The commissures-in-a-cage optionally acts as a skeleton to support prosthesis valve leaflets. In some embodiments the commissures-in-a-cage are optionally three commissures positioned at angles of 120 degrees apart on a circular plane of a diameter smaller than the native annulus (For additional details see a description of FIG. 16 below. The three commissures can optionally be made in a shape of straight struts, or as tapered struts with their thin portion pointing in a direction of the blood flow.

In some embodiments the commissure posts are optionally symmetrically distributed around a frame. In some embodiments the commissure posts are optionally distributed around the frame at locations corresponding to positions of native heart valve commissures.

The balcony is optionally constructed in such a way that it is larger in diameter than the native annulus, for a span of at least 100 degrees around a circumference of the cardiac valve support 140.

Reference is now made to FIGS. 1B and 1C, which are simplified illustrations of an example embodiment of the invention.

FIGS. 1B and 1C are intended to depict a flexible sheet acting as a seal against blood leaking back upstream between a cardiac valve support 150 and an annulus portion 153 of the natural heart.

FIGS. 1B and 1C depict a simplified illustration of an example embodiment of a cardiac valve support 150 for a prosthesis for a cardiac valve.

The example embodiment of a cardiac valve support 150 is depicted as including two general portions:

an upstream portion 151, also termed an onion, which is made to have at least some dimensions wider than the annulus portion 153 of the natural heart, preventing the cardiac valve support 150 from shifting downstream; and a downstream portion, also termed a balcony, which is made to have at least some dimensions wider than the annulus portion 153 of the natural heart, preventing the cardiac valve support 150 from shifting upstream.

The downstream portion of the example embodiment of FIGS. 1B and 1C includes a balcony railing 156, which is made to have at least some dimensions wider than the annulus portion 153 of the natural heart, preventing the downstream portion from shifting downstream, and a flexible sheet 152 154 around the cardiac valve support 150.

FIG. 1B depicts the natural heart during a time when blood flows downstream, which is depicted as down along the page, or at least blood is not under pressure to flow back upstream relative to the cardiac valve support 150.

In some embodiments a portion 154 of the flexible sheet 152 154 is optionally relaxed, optionally spanning a span from an inner diameter of the cardiac valve support 150 toward the balcony railing 156.

In some embodiments the portion 154 of the flexible sheet 152 154 is optionally attached, optionally sutured, to the inner diameter of the cardiac valve support 150. A general plane of the portion 154 of the flexible sheet 152 154 is optionally approximately parallel to a general plane of the natural cardiac annulus.

FIG. 1C depicts the natural heart during a time when blood is under pressure to flow back upstream relative to the cardiac valve support 150. The blood exerts pressure 158 on a portion 154 of the flexible sheet 152 154, and the portion 154 of the flexible sheet 152 154 is optionally free to bend against a wall of the natural heart and/or against the natural cardiac annulus, and prevent blood flow around the cardiac valve support 150.

In some embodiments there is a fabric which is sutured to an edge of the balcony at its outside circumference, and to the cardiac valve support 150, in a way which allows the fabric between the cardiac valve support 150 and the balcony to have a region, parallel to the native annulus, which is not sutured and is free. The free region potentially enables, as a result of blood pressure in the ventricle, the fabric to "bulge" at the free region and press against a sub-annulus region of the native cardiac valve. This optionally acts as a sealing mechanism such as depicted in FIG. 1C. Such a seal is potentially better than prior art seals, in which fabric is sutured to the anchoring component along its structure.

In some embodiments the flexible sheet comprises a biocompatible synthetic sheet.

In some embodiments the flexible sheet comprises a pericardium tissue sheet.

In some embodiments the flexible sheet comprises a woven fabric, and/or a perforated sheet perforated with small perforations, such as perforations smaller than 0.1 mm.

Reference is now made to FIGS. 1D and 1E, which are top view and side view images respectively, depicting an example embodiment of the invention.

FIGS. 1D and 1E are intended to show an example embodiment of a device 100 for artificial cardiac valve support and to identify sides of the device 100 which will be termed anterior 102 and posterior 104 sides throughout the present application. FIG. 1D is a side view of the device 100, and FIG. 1E is a bottom view.

Also identified are an inlet side, also termed an atrial side 106, and an outlet side, also termed a ventricle side 108, of an artificial cardiac valve which is designed to be supported by the artificial cardiac valve support.

FIG. 1D also identifies a location 105 at which, in an example embodiment, the device 100 is meant to approximately be at a native cardiac valve annulus.

Figure 2A:
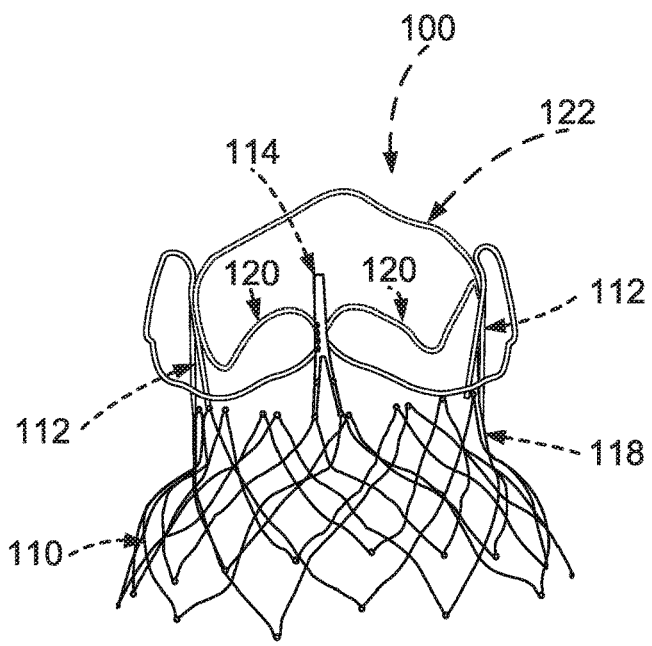
FIGS. 2A, 2B and 2C are images depicting the example embodiment of the device of FIGS. 1D and 1E from different viewpoints, intended to identify some components of the device.
Figure 2C:
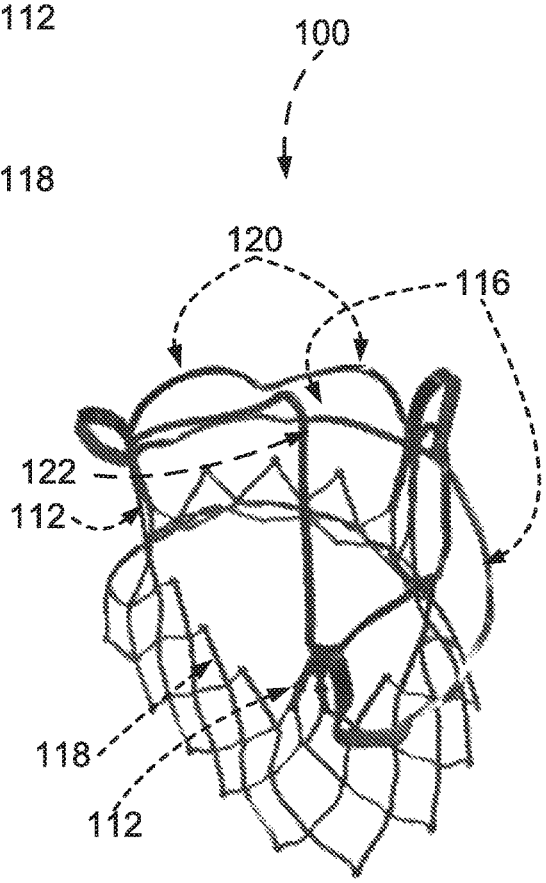
Figure 2B:
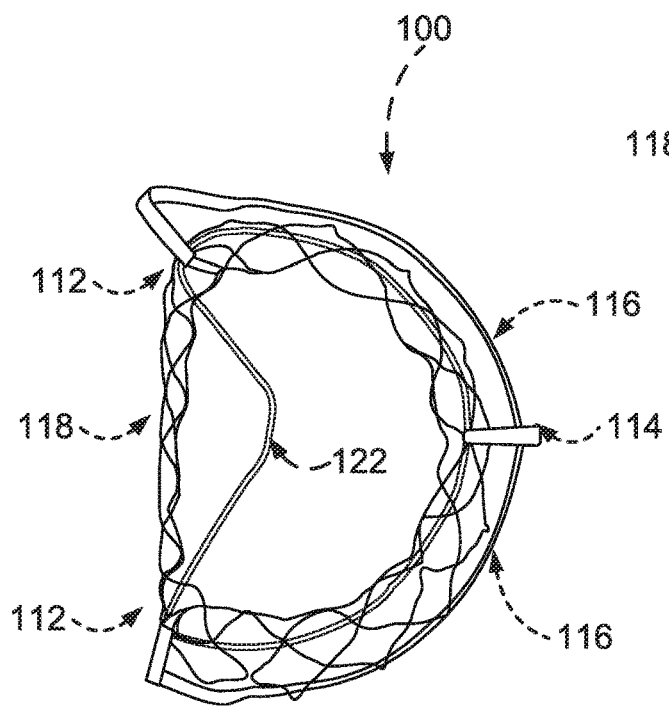

Reference is now also made to FIGS. 2A, 2B and 2C, which are images depicting the example embodiment of the device 100 of FIGS. 1D and 1E from different viewpoints, intended to identify some components of the device 100.

Components of the example embodiment of the device 100 may include one or more of:
a frame 110;
commissure posts 112;
a posterior extension 114;
a supporting arch 116;
a D-shaped frame section 118;
side ribs 120; and
a commissure arch (122).

In some embodiments, the frame 110 is designed to be larger in diameter than a native heart annulus, preventing a potential shifting of the device 100 downstream into a ventricle.

In some embodiments the commissure posts 112 are attached to the frame 110 at such a location so as to extend from the atrium into the ventricle at commissures of the natural heart valve.

In some embodiments, for example when the artificial valve is an artificial valve as described in US published patent application number 2010/0280606 of Naor and/or in PCT patent application number IL2014/050414 of Naor, the commissure posts 112 also support the artificial valve leaflets. The commissure posts 112 optionally support the valve leaflets along their length.

In some embodiments, three leaflets are used in the artificial valve, in which case the posterior extension 114 also act as a commissure post.

In some embodiments the posterior extension 114 is attached to the frame 110 so as to extend from the atrium into the ventricle downstream of the mitral valve annulus and partway back and out, optionally pushing a posterior leaflet of the natural mitral valve toward a ventricle wall.

In some embodiments the supporting arch 116 is connected to a downstream end of a first one of the commissure posts 112 to a downstream end of the posterior extension 114 to a downstream end of a second one of the commissure posts 112. The supporting arch 116 is optionally shaped so as to pushing the posterior leaflet of the natural mitral valve toward the ventricle wall along the length of the supporting arch 116. The supporting arch 116 spreads any back pressure which acts on the device 100 along some or all of the length of the supporting arch 116, lowering the pressure that is acting on the ventricle wall tissue.

In some embodiments the shape of the supporting arch 116 takes into account and accommodates the papillary muscles. This may be seen in FIG. 12, which is described below, where it may be seen that the papillary arch 116 includes a bend which provides space for accommodating the papillary muscle.

In some embodiments the D-shaped frame section 118, when placed at a natural cardiac valve annulus, potentially acts to reshape a diseased natural cardiac valve annulus to a healthy shape. In some embodiments the D-shaped frame section 118 is shaped as a lumen having a length, along a central axis of the lumen, sufficient to enable the D-shaped frame section 118 to seal against a natural valve annulus even when the natural valve annulus is not exactly planar, and/or when the device 100 is somewhat tilted.

In some embodiments the D-shaped frame section 118, when placed at a natural cardiac valve annulus, potentially acts to seal a possibility of blood leaking back around the device 100 by pressing against the sides of the natural cardiac valve annulus.

In some embodiments the side ribs 120 stiffen and strengthen the device 100, more specifically the commissure posts 112 and the posterior extension 114.

In some embodiments the commissure arch 122 stiffens and strengthens the device 100, more specifically the commissure posts 112.

Figure 3:
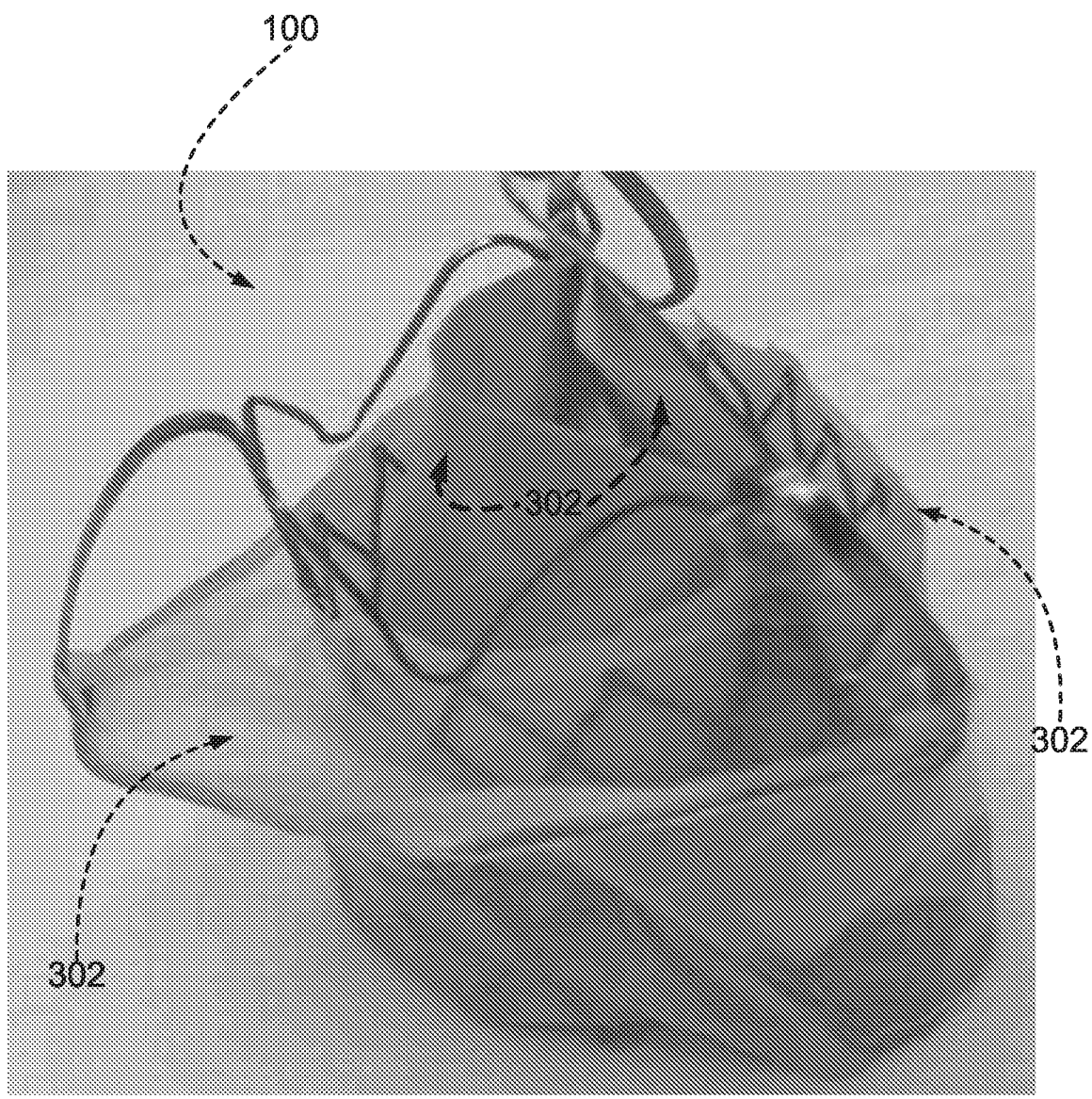
FIG. 3 is an image depicting the example embodiment of the device of FIGS. 1D and 1E, additionally clad with flexible sheets and supporting an example embodiment of an artificial valve.

Reference is now also made to FIG. 3, which is an image depicting the example embodiment of the device 100 of FIGS. 1D and 1E, additionally clad with flexible sheets and supporting an example embodiment of an artificial valve.

FIG. 3 is intended to depict optional flexible sheets which assist in sealing the device 100 against potential back leakage of blood around the device 100. FIG. 3 is also intended to depict an example embodiment of a bi-leaflet valve constructed of flexible sheet(s).

FIG. 3 depicts: the device 100; a first flexible sheet 302 attached to an outside of the device 100; and a bi-leaflet valve 302 constructed of one or more flexible sheets.

The first flexible sheet 302, attached to an outside of the device 100, potentially acts to seal a possibility of blood leaking back around the device 100.

The bi-leaflet valve 304 is an example embodiment of a possible valve for use as an artificial cardiac valve, supported by an embodiment of the cardiac valve support device 100.

In some embodiments, the flexible sheet is a sheet of bio-compatible material. In some embodiments, the flexible sheet is a sheet of pericardium.

Figure 4:
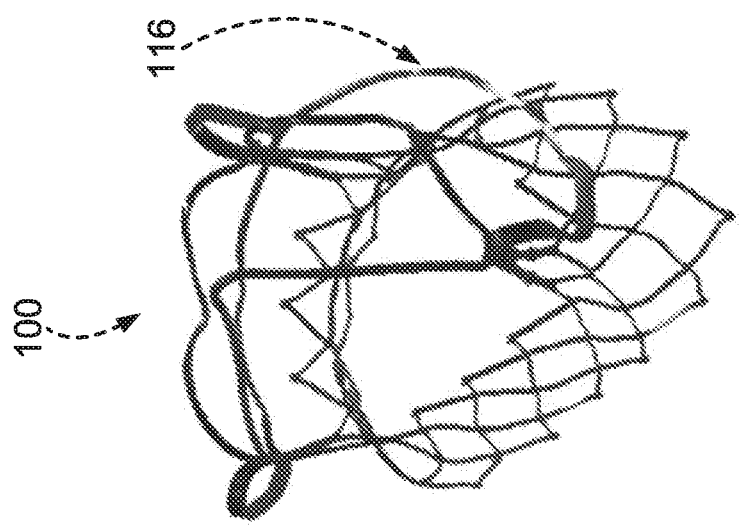
FIG. 4 is an image depicting the example embodiment of the device of FIGS. 1D and 1E.

Reference is now also made to FIG. 4 which is an image depicting the example embodiment of the device 100 of FIGS. 1D and 1E.

FIG. 4 is intended to depict the supporting arch 116, also depicted in FIGS. 2B and 2C, from a viewpoint which emphasizes the supporting arch 116.

In some embodiments, the supporting arch 116 is an extension to the frame 110 of FIG. 2A, optionally constructed of 3 legs—the two commissure posts 112 and the posterior extension 114—joined by two arch sections.

Together, the supporting arch 116 forms an open C shape, optionally larger in diameter than an artificial cardiac valve supported by the device 100. In some embodiments, a distance between an inlet portion of the artificial cardiac valve and an outlet portion of the artificial cardiac valve is approximately a length of the native annulus.

Figure 5:
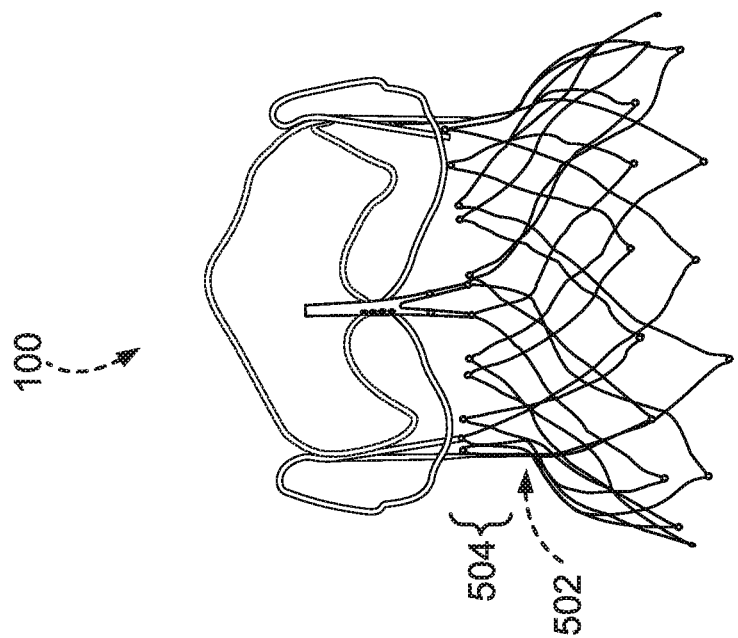
FIG. 5 is an image depicting the example embodiment of the device of FIGS. 1D and 1E.

Reference is now also made to FIG. 5 which is an image depicting the example embodiment of the device 100 of FIGS. 1D and 1E.

FIG. 5 is intended to depict the supporting arch 116, also depicted in FIGS. 2B and 2C, from a viewpoint which emphasizes a spatial relation of the supporting arch 116 with an approximate location 502 of a native annulus.

In some embodiments, the arch is located 5-15 mm (reference 504) from the approximate location 502 of the native annulus towards the outlet side.

In some embodiment, an anterior side of the supporting arch 116 is open. The supporting arch 116 optionally causes the heart anatomy to form a "step" under the native annulus on a side of the ventricle. Optionally, the supporting arch 116 anchors into that step, which can spread a force potentially caused on the device 100 by blood pressure. In spreading the force, pressure is reduced, and a chance of piercing or bruising the anatomy by the device 100 is potentially lowered.

Figure 6C:
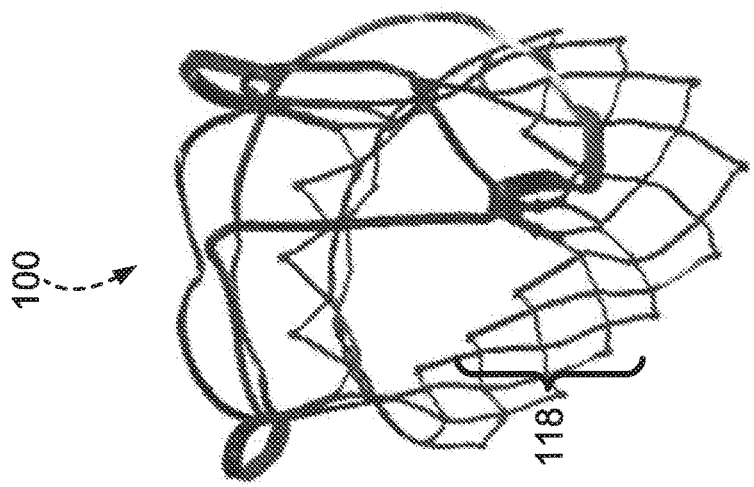
FIGS. 6B and 6C are images depicting the example embodiment of the device of FIG. 6A.
Figure 6B:
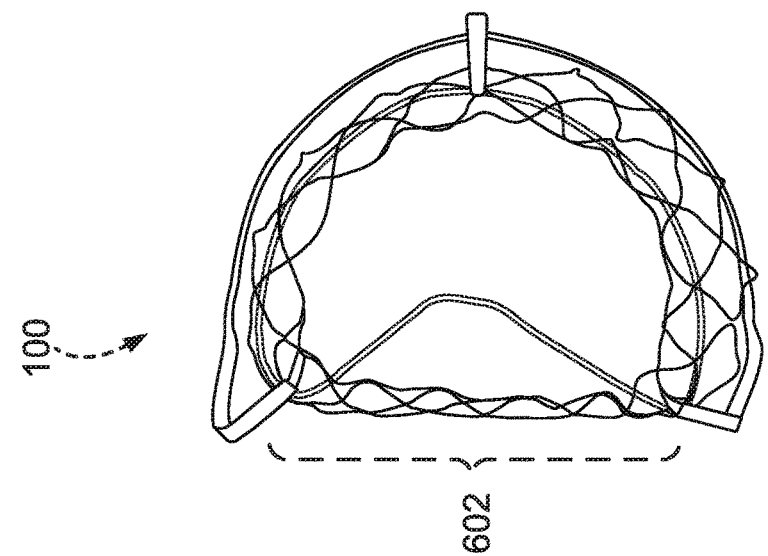
Figure 6A:
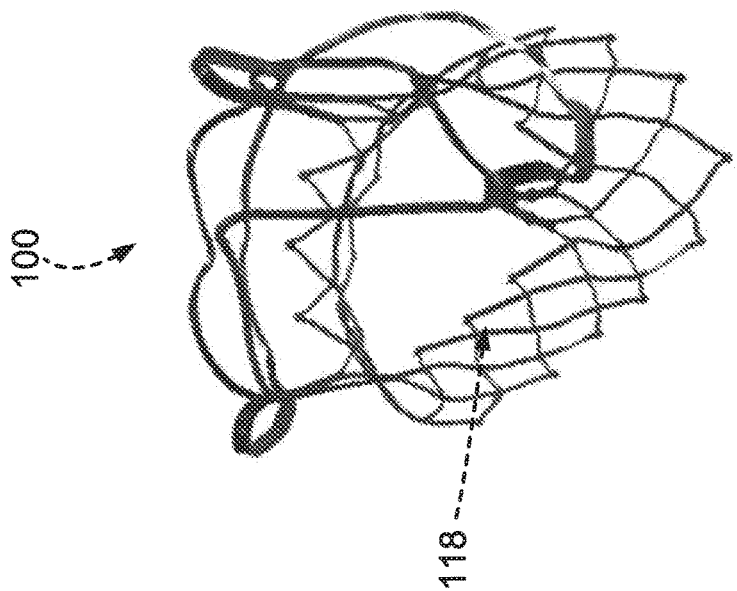
FIG. 6A is an image depicting the example embodiment of the device of FIGS. 1D and 1E.

Reference is now also made to FIG. 6A which is an image depicting the example embodiment of the device 100 of FIGS. 1D and 1E.

FIG. 6A is intended to depict the D-shaped frame section 118, also depicted in FIGS. 2A, 2B and 2C, from a viewpoint which emphasizes the D-shaped frame section 118.

In some embodiments, especially when used in a mitral valve, the D-shaped frame section 118 is optionally used for re-shaping a native mitral valve annulus. The re-shape optionally brings the native mitral valve annulus close to its healthy shape. The D-shaped frame section 118 potentially enables sealing of the device 100 against a native annulus. The straight side of the D-shape potentially enables the sealing without pushing the native anterior leaflet out into a path of blood from the ventricle to the aorta, which might cause full or partial blocking of the aorta.

Reference is now also made to FIGS. 6B and 6C, which are images depicting the example embodiment of the device 100 of FIG. 6A.

FIG. 6B is a top view, intended to depict the D-shaped frame section 118, from a viewpoint which emphasizes a straight section 602 in the D-shaped frame section 118. FIG. 6C shows the same view as FIG. 6A, and is intended to identify the D-shaped frame section 118.

In some embodiments the D-Shape frame section 118 includes a continuation of the "D"-Shape into an outlet portion on one side and into an inlet portion on other side.

One purpose of this almost flat area is to continue the "D"-shape's sealing. The sealing is believed to be enabled by keeping a flat part of the D-Shape frame section 118 against a flat "aortic-mitral continuation" portion of the annulus of a mitral valve. By virtue of the length of the lumen of the D-shaped frame section 118 the seal is maintained even if the device 100 has tilted or situated just approximately in place.

Another purpose of the semi-flat D-shaped design is to prevent native anatomy on either an atrial side or a ventricle side from pushing the D-shaped frame section 118 and changing its location within the mitral valve.

Figure 7:
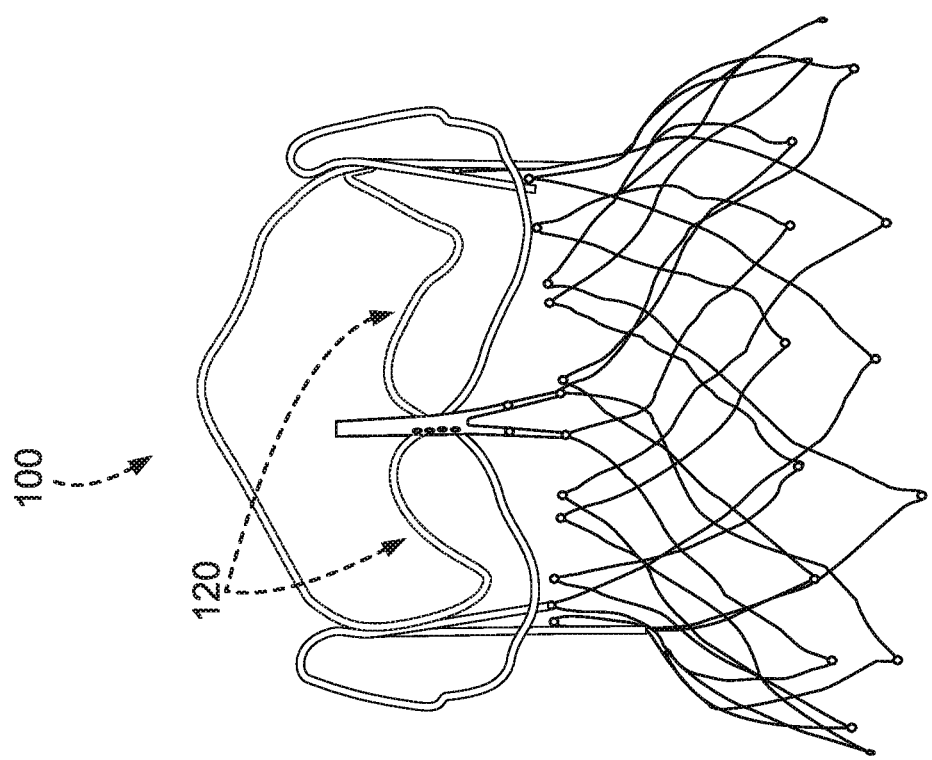
FIG. 7 is an image depicting the example embodiment of the device of FIGS. 1D and 1E.

Reference is now also made to FIG. 7 which is an image depicting the example embodiment of the device 100 of FIGS. 1D and 1E.

FIG. 7 is intended to depict the side ribs 120, also depicted in FIG. 2A, from a viewpoint which emphasizes the side ribs 120.

In some embodiments the side ribs 120 are triangular struts, stretching between the commissure posts 112 and the posterior extension 114. In some embodiments the side ribs 120 are located toward an outlet portion of the device 100. One function of the side ribs 120 is to strengthen the commissure posts 112 and the posterior extensions 114. A second function of the side ribs 120 is to help stabilize the device 100 and add support to the cardiac anatomy.

Figure 8A:
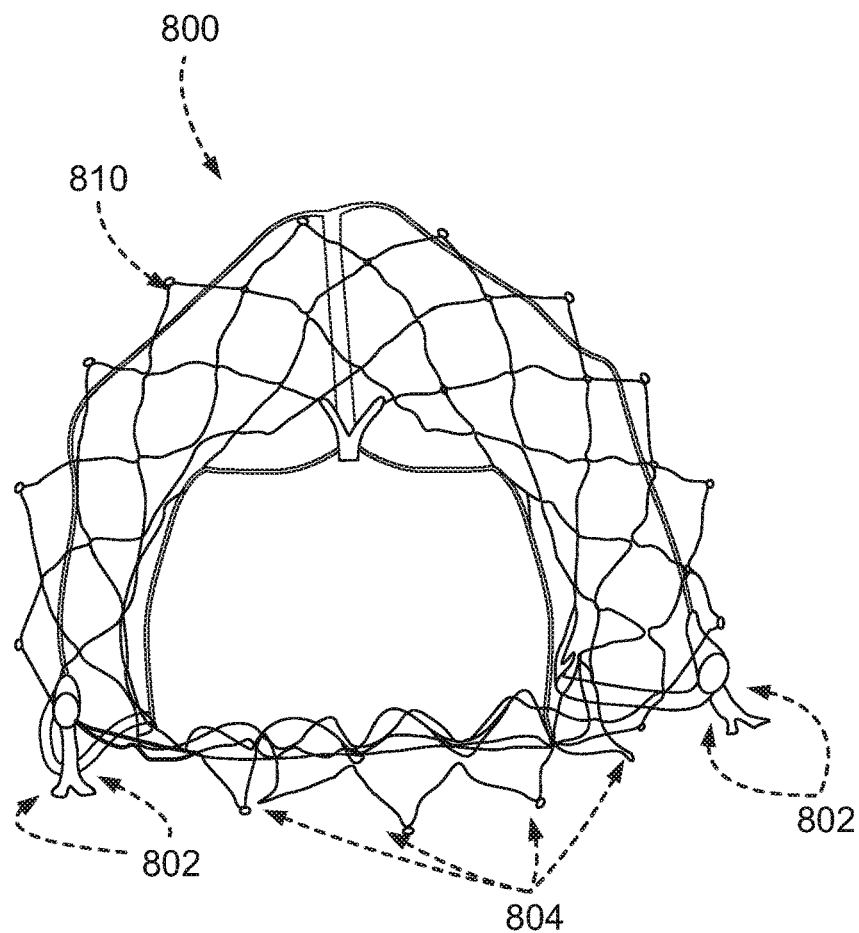
FIG. 8A is an image depicting an example embodiment of the invention.

Reference is now also made to FIG. 8A which is an image depicting an example embodiment of the invention.

FIG. 8A is intended to depict optional hooks 802 and anterior leaflet grabbers 804, attached to a device 800 for artificial cardiac valve support.

FIG. 8A depicts a frame 810.

In some embodiments hooks 802 are optionally attached to the frame 810, close to a location of a straight portion of a D-shaped section.

In some embodiments, the hooks 802 are optionally used as trigon anchors. In such embodiments, the hooks 802 are optionally embedded into parts of the cardiac anatomy named trigons, and optionally act as part of the anchoring of the device 800 within a mitral valve.

In some embodiments, the hooks 802 are optionally used as anterior leaflet hooks, each one of the anterior leaflets hooks configured to engage chordae connecting to the native anterior leaflet and pull the anterior leaflet in opposing directions.

In some embodiments anterior leaflet grabbers 804 are attached to the device 800, optionally along the straight portion of a D-shaped section.

In some embodiments, the anterior leaflet grabbers 804 are optionally folded struts such as are included in the stent-like frame 810: Optionally, a native anterior leaflet of a mitral valve is caught by the folded struts (the anterior leaflet grabbers 804) and is optionally pulled and folded to the straight portion of the D-shaped section. In some embodiments, the anterior leaflet chords are pulled by the anterior leaflet grabbers 804. In some embodiments the grabbing of the anterior leaflet provides an additional anchoring mechanism of the device 800 to cardiac anatomy. In some embodiments the grabbing of the anterior leaflet potentially keeps the anterior leaflet from blocking blood flow toward the aorta.

Figure 8B:
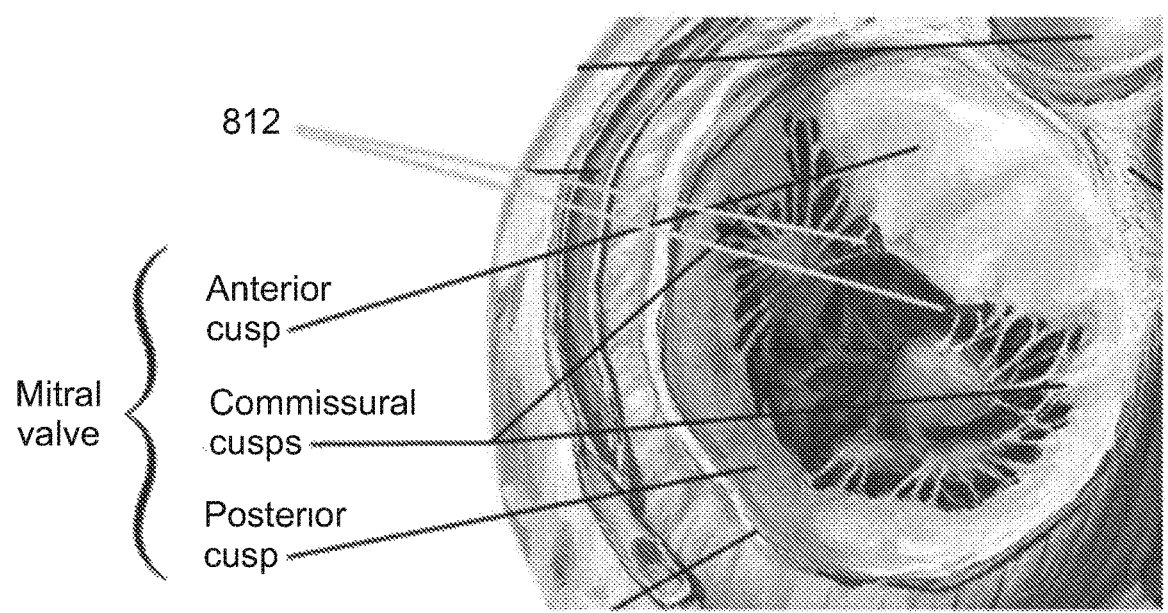
FIG. 8B is a line drawing of a heart depicting an example location for hooks to engage an anterior leaflet of a mitral valve according to an example embodiment of the invention.

Reference is now made to FIG. 8B, which is a line drawing of a heart depicting an example location for hooks to engage an anterior leaflet of a mitral valve according to an example embodiment of the invention.

FIG. 8B depicts possible locations 812 for the hooks 802 of FIG. 8A to grasp an anterior leaflet and stretch the leaflet.

Figure 9:
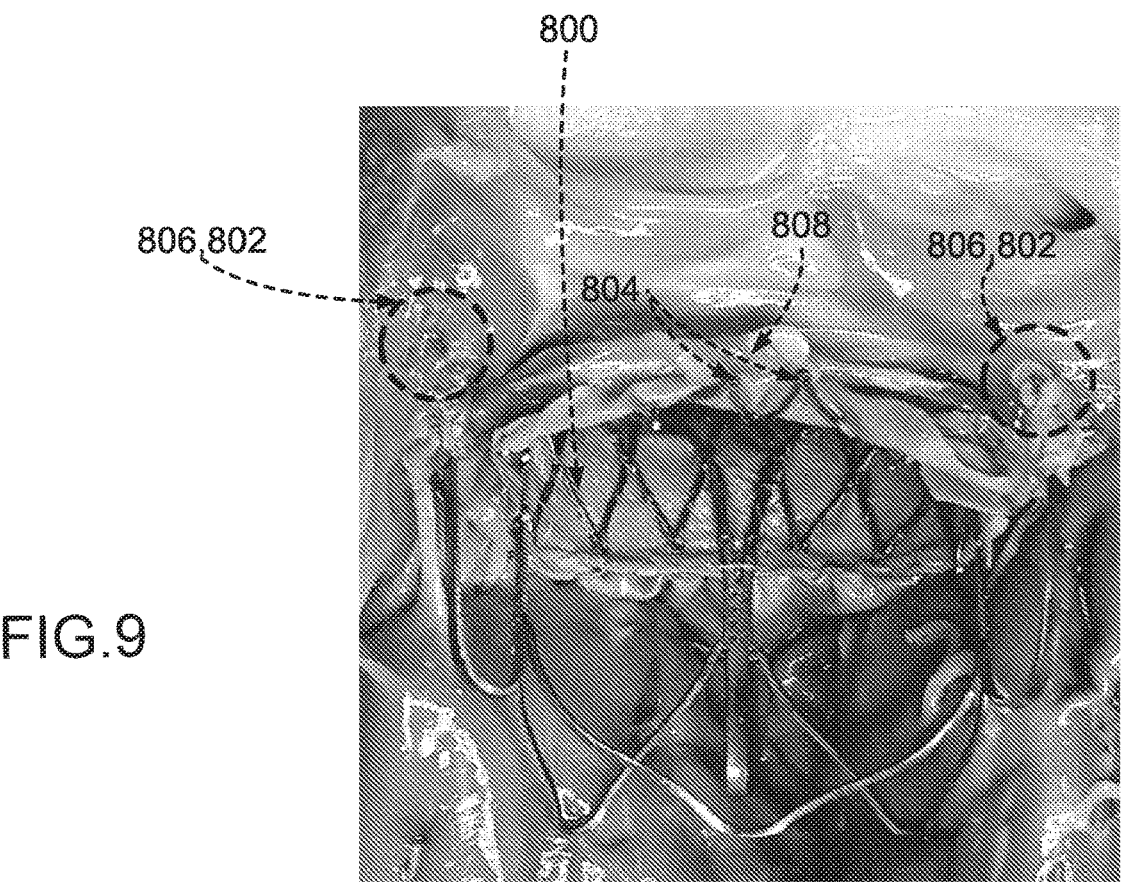
FIG. 9 is an image depicting the device of FIG. 8A in place within a mitral valve.

Reference is now also made to FIG. 9 which is an image depicting the device 800 of FIG. 8A in place within a mitral valve.

It is noted that the image is of a pig's heart, which also has valves similar to the mitral and aortic valves of a human.

FIG. 9 is intended to depict the hooks 802 and the anterior leaflet grabbers 804 in relation to a heart. FIG. 9 depicts a photograph taken through an incision in a right ventricle and through a septum, showing a left ventricle having an implanted device 800.

Circles 806 mark locations named trigons in the heart. The hooks 802 anchor the device.

An anterior leaflet 808 is depicted caught within folded struts, termed herein the anterior leaflet grabbers 804.

FIG. 9 depicts the device 800 positioned within a native valve, showing the anterior leaflet grabbers 804 lifting the anterior leaflet of the native valve, thus clearing the LVOT free for blood flow.

Figure 10:
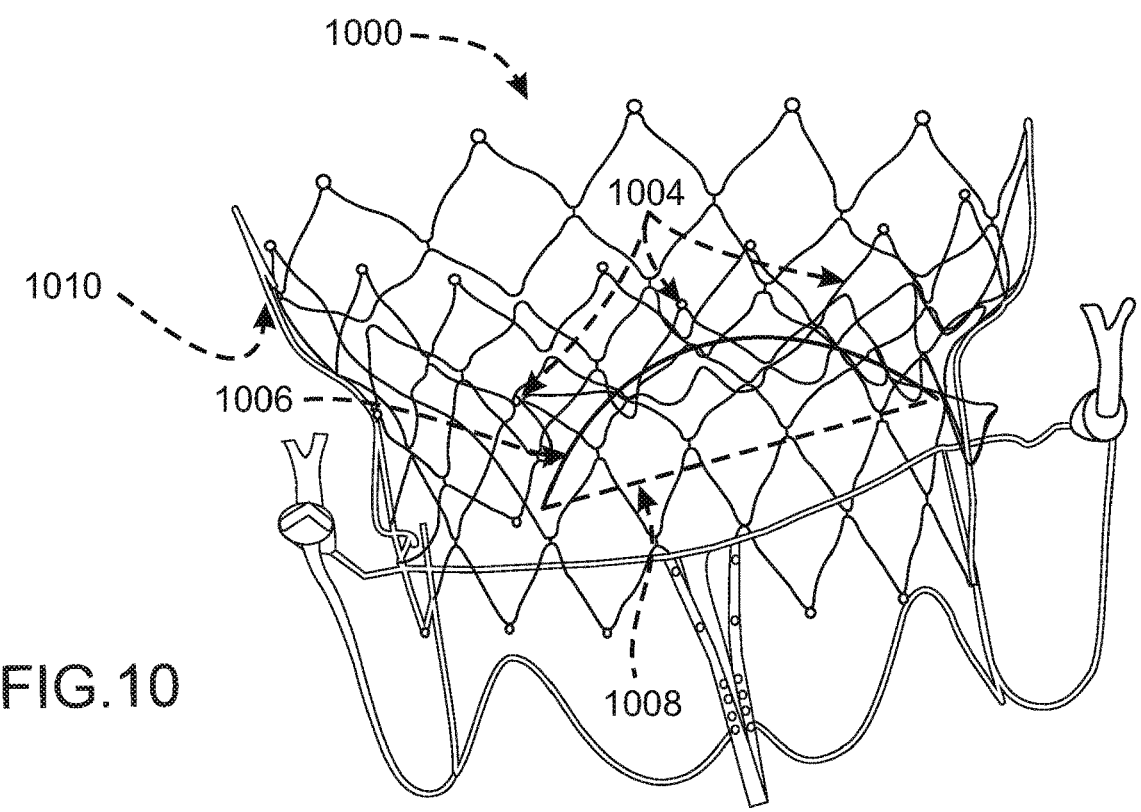
FIG. 10 is an image depicting an example embodiment of the invention.

Reference is now also made to FIG. 10 which is an image depicting an example embodiment of the invention.

FIG. 10 is intended to depict anterior leaflet grabbers 1004, attached to a device 1000 for artificial cardiac valve support.

FIG. 10 depicts the device 1000, a frame 1010, and anterior leaflet grabbers 1004 are attached to the device 1000.

FIG. 10 depicts the device 1000 from a direction which would show an aorta located behind the anterior leaflet grabbers, were the heart depicted in FIG. 10. The anterior leaflet grabbers, when covered with pericard, may block blood flow from a left ventricle the aorta. In FIG. 10, the anterior leaflet grabbers are folded, and allow free blood flow from the left ventricle to the aorta. FIG. 10 shows a line 1006 following the folded struts of the anterior leaflet grabbers relative to a second line 1008 showing if the struts were not folded. It is noted that using folded struts rather than un-folded struts for the anterior leaflet grabbers potentially results in an open blood flow to the aorta.

As described above with reference to FIG. 9, the hooks 802 and anterior leaflet grabbers 804 hold an anterior leaflet and pull it against an anterior side of the frame 810 and optional pericard skirt. This potentially results in a sealing of the anterior region of the device to native mitral valve interface.

Figure 11:
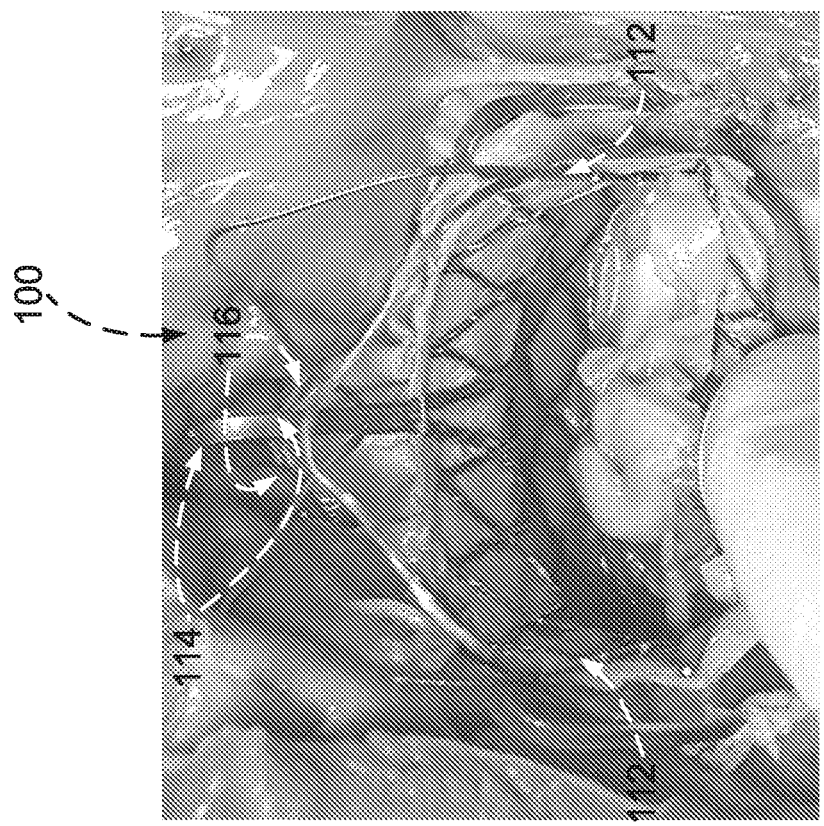
FIG. 11 is an image depicting an example embodiment of the invention in place within a mitral valve.

Reference is now also made to FIG. 11 which is an image depicting an example embodiment of the invention in place within a mitral valve.

FIG. 11 is intended to depict the posterior extension 114 and the supporting arch 116 of, for example, FIGS. 2A, 2B and 2C, in relation to a heart. FIG. 11 depicts a photograph taken from a left ventricle apex toward a mitral valve, showing a left ventricle having an implanted device 100.

FIG. 11 depicts the posterior extension 114 extending between papillary muscles of the heart.

FIG. 11 also depicts the supporting arch 116, optionally covered by a flexible sheet, resting against a wall of the left ventricle. The supporting arch 116 is depicted assisting in anchoring the device 100 in the heart and in sealing against leakage of blood between the device 100 and the heart.

The supporting arch 116 connects the commissure posts 112 with the posterior extension 114. A diameter of the supporting arch 116 is optionally larger than a diameter of the native mitral annulus. During systole, blood pressure pushes the device 100 upwards toward the atrium. In such embodiments where the supporting arch 116 diameter is larger than the diameter of the native mitral annulus, the supporting arch 116 is pushed against the left ventricle wall, and assists in anchoring the device 100. In addition, the force that pushes the supporting arch 116 against left ventricle tissue results in potentially sealing against leakage.

Figure 12:
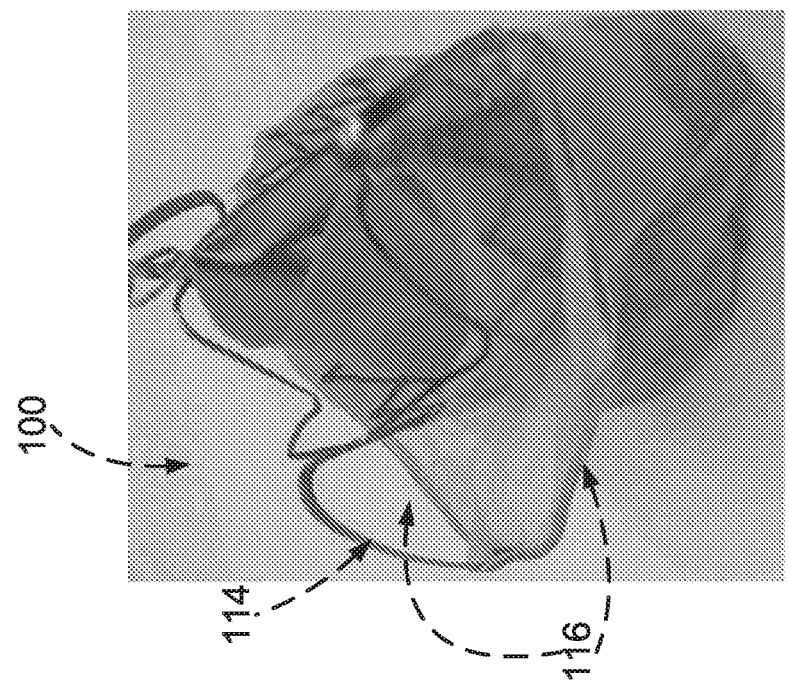
FIG. 12 is an image depicting an example embodiment of the invention outside of a heart.

Reference is now also made to FIG. 12 which is an image depicting an example embodiment of the invention outside of a heart.

FIG. 12 is intended to depict the posterior extension 114 and the supporting arch 116 of, for example, FIGS. 2A, 2B and 2C, from a viewpoint which accentuates the posterior extension 114 and the supporting arch 116.

Figure 13:
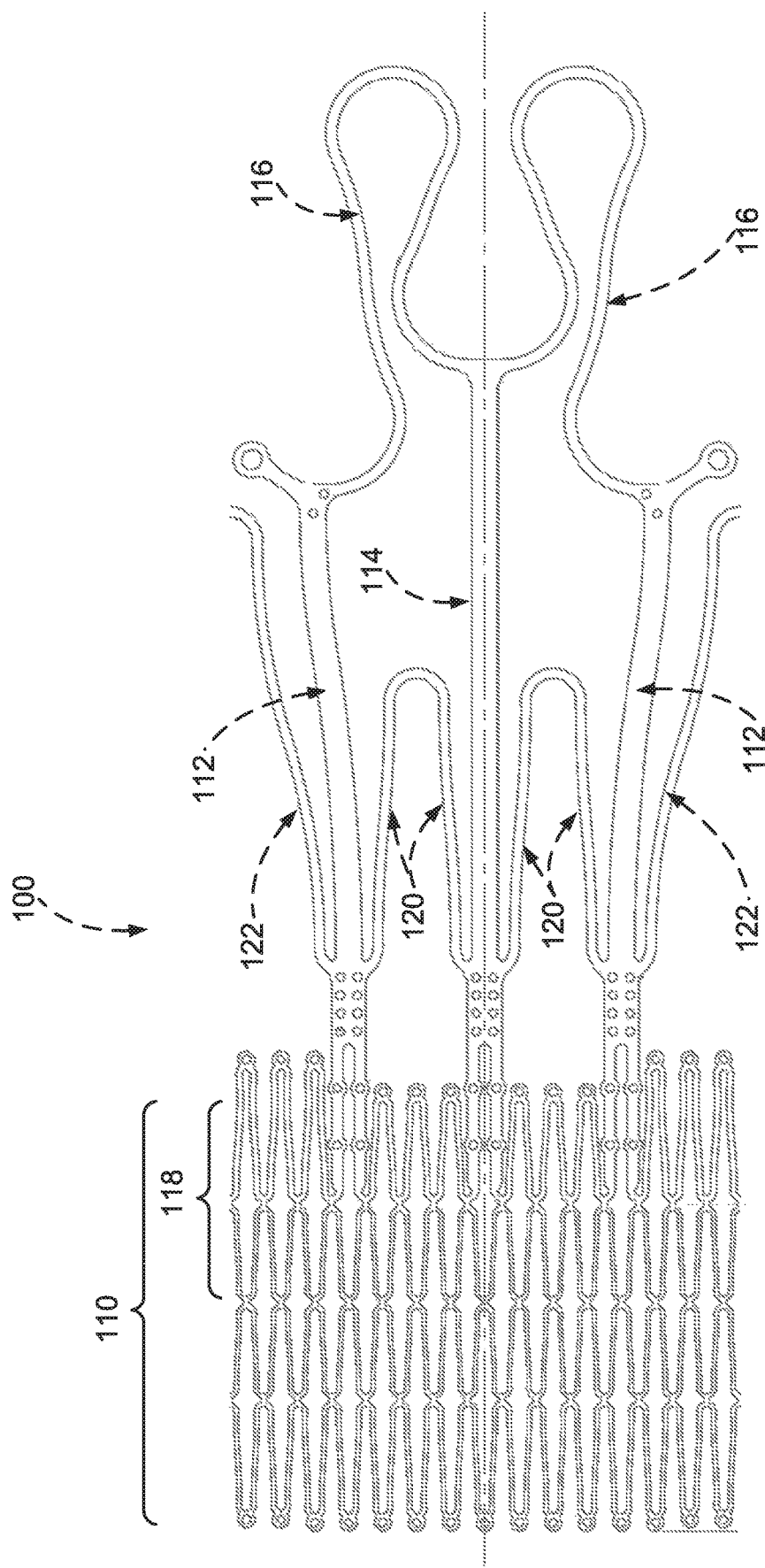
FIG. 13 is a flat two-dimensional mechanical drawing of the example embodiment of the device, intended to identify some components of the device.

Reference is now also made to FIG. 13, which is a flat two-dimensional mechanical drawing of the example embodiment of the device 100, intended to identify some components of the device 100.

FIG. 13 depicts the frame 110; the commissure posts 112; the posterior extension 114; the supporting arch 116; the D-shaped frame section 118; the side ribs 120; and the commissure arch (122).

Figure 14:
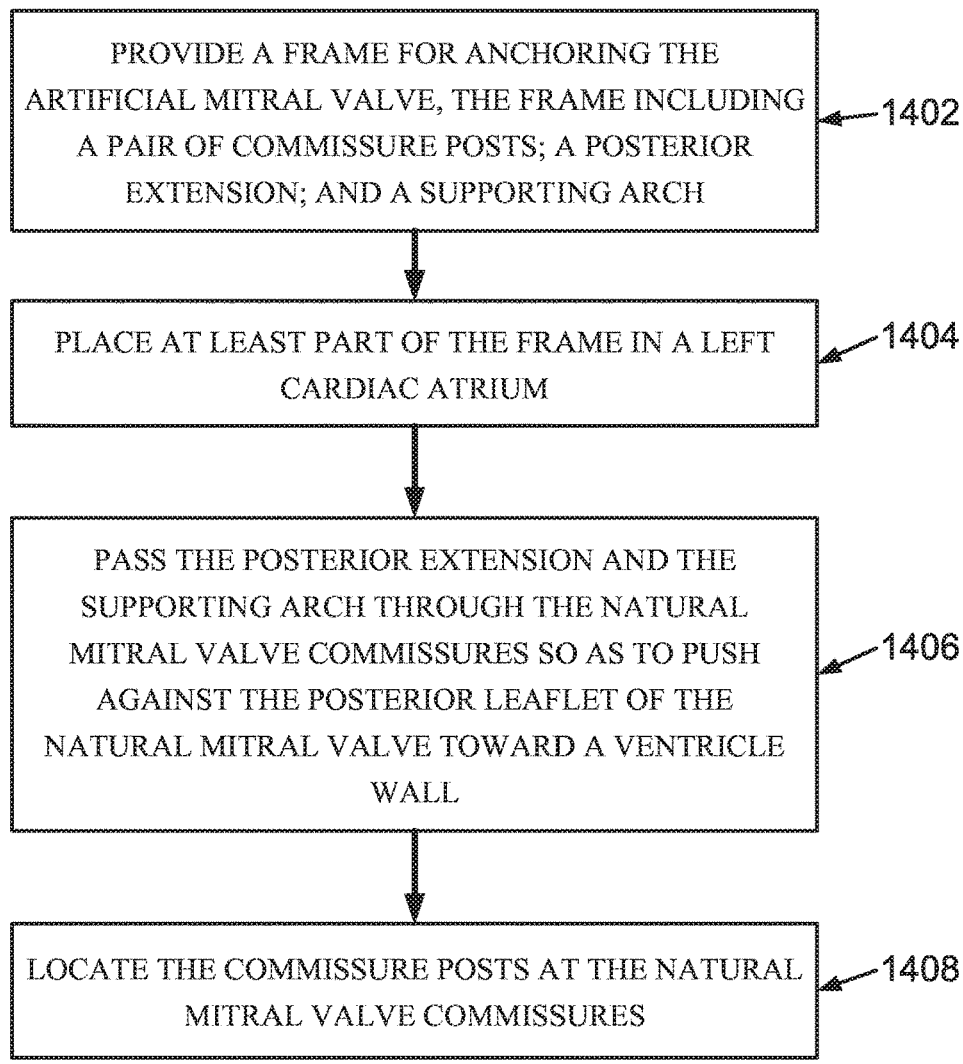
FIG. 14 is a simplified flowchart illustration of a method of supporting an artificial mitral valve according to an example embodiment of the invention.

Reference is now also made to FIG. 14, which is a simplified flowchart illustration of a method of supporting an artificial mitral valve according to an example embodiment of the invention.

The method illustrated by FIG. 14 includes:
providing a frame for anchoring the artificial mitral valve, configured to be placed upstream of a natural mitral valve annulus and shaped to be able to expand to a diameter larger than the natural mitral valve annulus, to prevent the frame from shifting downstream of the natural mitral valve annulus (1402),
the frame including:
a pair of commissure posts attached at one end to the frame, the commissure posts configured to extend downstream of a mitral valve annulus through the commissures of the natural mitral valve;
a posterior extension attached at a first end to the frame, the posterior extension configured to extend downstream of the mitral valve annulus and partway back and out, pushing a posterior leaflet of the natural mitral valve toward a ventricle wall; and
a supporting arch attaching a downstream end of a first one of the commissure posts to a downstream end of the posterior extension to a downstream end of a second one of the commissure posts,
placing at least part of the frame in a left cardiac atrium (1404);
passing the posterior extension and the supporting arch through the natural mitral valve commissures so as to push against the posterior leaflet of the natural mitral valve toward a ventricle wall (1406); and
locating the commissure posts at the natural mitral valve commissures (1408).

Figure 15:
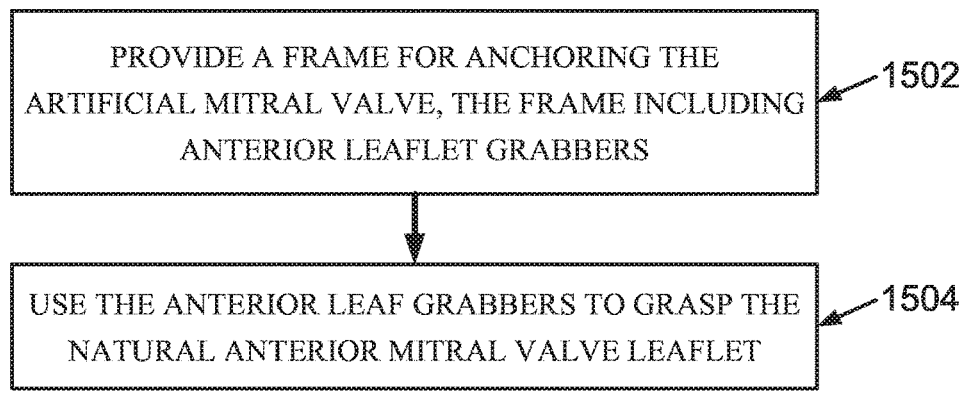
FIG. 15 is a simplified flowchart illustration of a method of supporting an artificial mitral valve according to another example embodiment of the invention.

Reference is now also made to FIG. 15, which is a simplified flowchart illustration of a method of supporting an artificial mitral valve according to another example embodiment of the invention.

The method illustrated by FIG. 15 includes:
providing a frame for anchoring the artificial mitral valve, configured to be placed upstream of a natural mitral valve annulus and shaped to expand larger than the natural mitral valve annulus to prevent the frame from shifting downstream of the natural mitral valve annulus (1502); the frame further comprising anterior leaflet grabbers, each one of plurality of anterior leaflet grabbers comprising one end attached to the frame and one end configured to grasp an anterior leaflet of the natural mitral valve,
using the anterior leaf grabbers to grasp the natural anterior mitral valve leaflet (1504).

Figure 16:
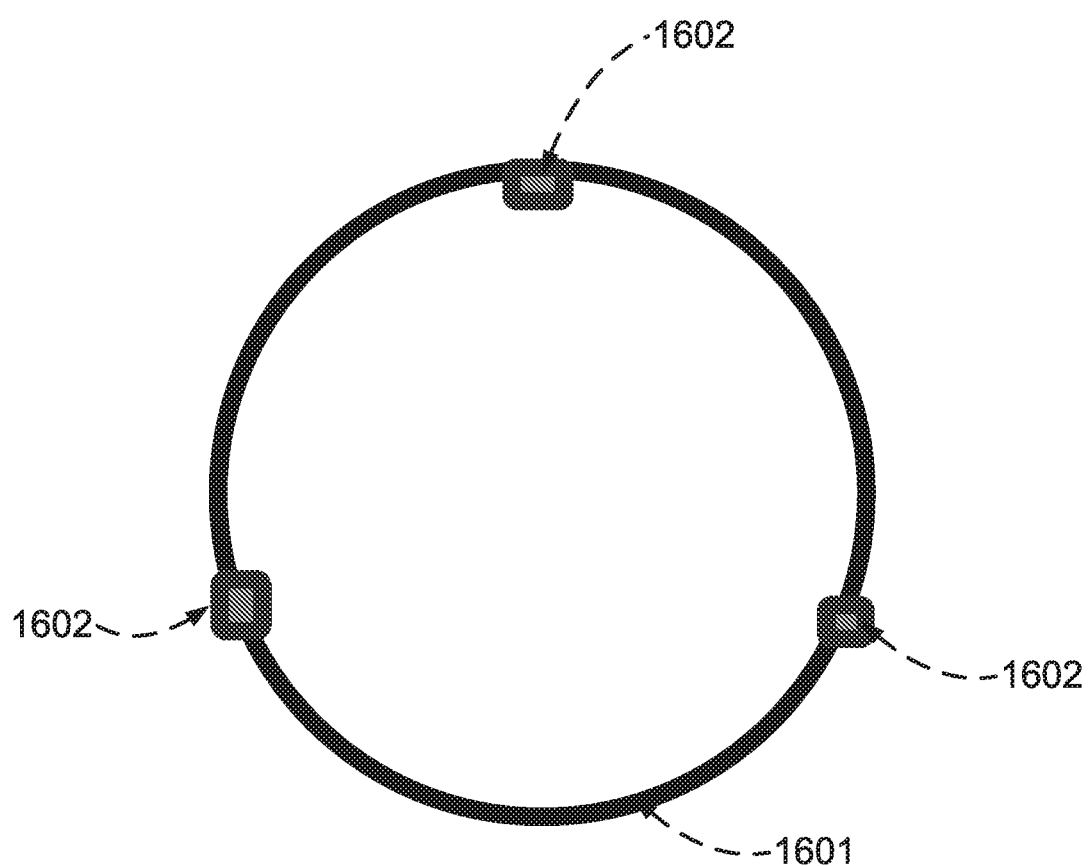
FIG. 16 is a simplified illustration of a cross section of commissures-in-a-cage according to an example embodiment of the invention.

Reference is now made to FIG. 16, which is a simplified illustration of a cross section of commissures-in-a-cage according to an example embodiment of the invention.

FIG. 16 depicts a cross-section of a cardiac valve support 1601, similar to the cardiac valve support 140 of FIG. 1A, with three prosthetic valve supports 1602, termed herein commissures 1602 or balcony commissures 1602. The commissures 1602 are not to be confused with commissures of a natural cardiac valve, as they are components of the artificial cardiac valve support 1601.

The three commissures potentially act as a skeleton to hold and support prosthesis valve leaflets. The commissures are optionally positioned at angles of 120 degrees apart on a plane of a section of the cardiac valve support 1601 having a diameter smaller than that of the native cardiac valve annulus. The three commissures may optionally be made as straight struts or as tapered struts with their thin portion pointing in a direction of the blood flow.

Reference is now made to FIGS. 17A, 17B and 17C, which are simplified illustrations of a cardiac valve support 1700 according to an example embodiment of the invention.

FIG. 17A is an isometric view, FIG. 17B is one side view, and FIG. 17C is another, perpendicular side view, of the cardiac valve support 1700.

FIGS. 17A-17C depict an example embodiment which has: a petal configuration on an upstream portion 1702 of the cardiac valve support 1700; three artificial commissures 1704 for attaching an artificial cardiac valve; three strut supports 1706 located between the three commissures 1704; and two levels of arcs 1708 between the commissures 1704 and the strut supports 1706, which optionally also act as an anchoring downstream portion, also termed a balcony.

In some embodiments the upstream portion 1702 resembles a "D" shape design as described above, which potentially enables free flow of blood through a cardiac valve.

In some embodiments the arcs 1708 optionally extend radially outward from a longitudinal axis of the cardiac valve support 1700, so as to span a larger diameter than a diameter of the natural cardiac valve annulus.

In some embodiments the arcs 1708 optionally serve for anchoring the cardiac valve support 1700 and/or sealing the cardiac valve support 1700 against blood flow upstream around the cardiac valve support 1700.

In the configuration depicted in FIGS. 17A-D, the atrium part or onion may be either a mesh, or stent like, and/or be shaped as petals. There are optionally six posts, three of which optionally act as commissures 1704, in order to strengthen a cage which supports the three commissures 1704. In some embodiments, the arcs 1708 that support the commissures 1704 are bent outward in order to potentially act as anchoring mechanisms and/or sealing mechanisms.

Reference is now made to FIG. 17D, which is a cross-sectional side view of the cardiac valve support 1700 in location in a natural cardiac valve 1712.

FIG. 17D depicts a sealing mechanism effected by native leaflets 1710 which are pushed aside and optionally fold around the arcs 1708. An anchoring mechanism is potentially also effected by the arcs 1708 which press on the heart (ventricle) walls, optionally pressing through the native leaflets 1710, and potentially prevents shifting of the cardiac valve support 1700 upstream of the natural cardiac valve 1712.

Figure 18B:
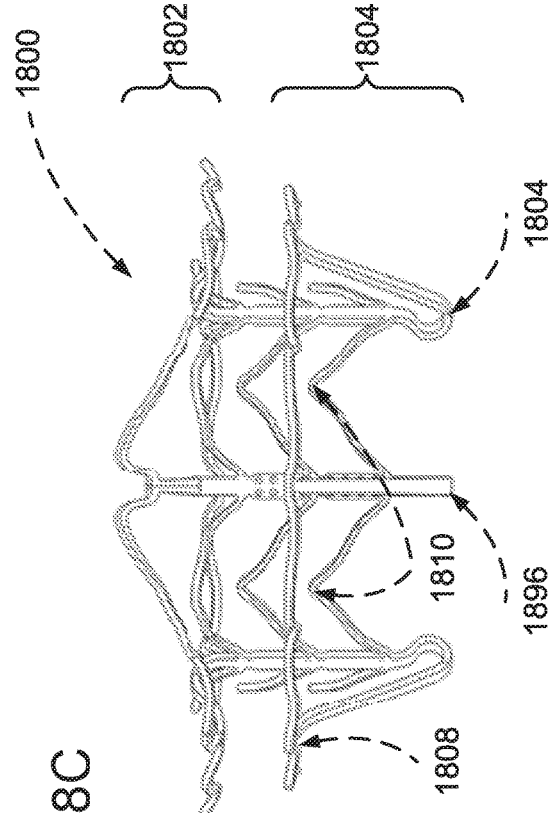
FIGS. 18A, 18B and 18C are simplified illustrations of a cardiac valve support according to an example embodiment of the invention.
Figure 18C:
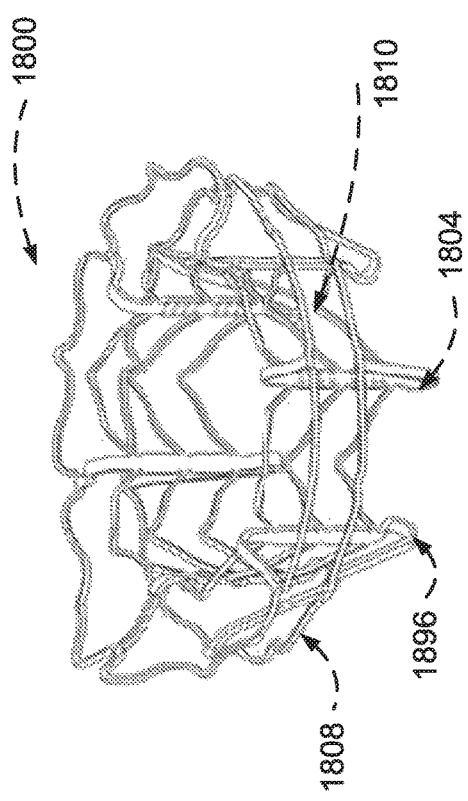
Figure 18A:
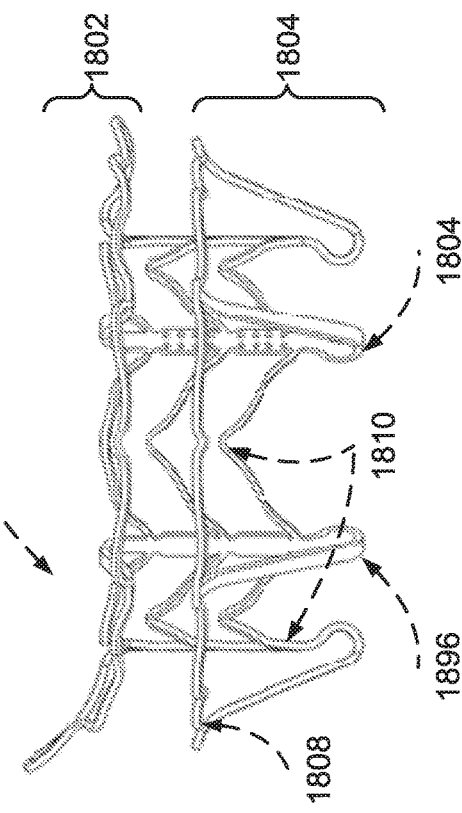

Reference is now made to FIGS. 18A, 18B and 18C, which are simplified illustrations of a cardiac valve support 1800 according to an example embodiment of the invention.

FIG. 18A is an isometric view, FIG. 18B is one side view, and FIG. 18C is another, perpendicular side view, of the cardiac valve support 1800.

FIGS. 18A-18C depict an example embodiment which has: an upstream, also termed onion, portion 1802 of the cardiac valve support 1800; three artificial commissure posts 1804 for attaching an artificial cardiac valve; three strut supports 1806 located between the three commissures 1804; arcs 1810; and a balcony 1808 for anchoring the cardiac valve support 1800 against shifting upstream.

FIGS. 18A-18C depict an embodiment in which the arcs 1810 are not extended outward further than the balcony 1808, and so do not serve as an anchoring mechanism. The commissure posts 1804 and/or the struts supports 1806 are made longer and are bent outward and up toward the upstream portion 1802 so as to form support for the balcony 1808. In some embodiments the commissure posts 1804 and/or the struts supports 1806 are optionally bent and optionally tilted back inward, potentially decreasing an overall diameter which the cardiac valve support 1800 can be folded, potentially aiding insertion via a catheter.

Reference is now made to FIGS. 19A, 19B, 19C and 19D, which are simplified illustrations of a cardiac valve support according to an example embodiment of the invention.

FIG. 19A is a side view and FIG. 19B is an isometric view of an upstream, onion, portion 1902 of a cardiac valve support.

FIG. 19C is an isometric view and FIG. 19D is a side view of a downstream, balcony, portion 1904 of the cardiac valve support.

FIGS. 19A-19D demonstrate an option which is possible with all embodiments described in the present application, in which the upstream portion 1902 and the downstream portion 1904 are, at least initially, produced separately from each other. The two portions may optionally be attached to each other before insertion into a patient, and having two portions potentially enables producing different cardiac valve supports which may include different styles of upstream portions and downstream portion as depicted within the present application. The two portions may optionally be attached to each other by welding, such as electric welding and/or laser welding, or by suturing together similarly to a suturing of a flexible sheet to the cardiac valve support. Additional methods of attaching the two portions include crimping and/or clamping a tube and/or folding a material such as metal around mating sections such as posts in the two portions and/or inserting pins into designated holes in mating sections and welding or pinning the portions.

FIGS. 19A and 19B depict a configuration in which an upstream portion 1902, an onion, is made in the form of mesh. In some embodiments the mesh may optionally be made at different densities of cells in order to control, that is, decrease or increase, stiffness of the onion. In some embodiments the onion optionally includes three posts at its downstream side which can acts as commissure posts 1908, or in order to connect the upstream portion 1902 to the downstream portion 1904. In some embodiments the three commissure posts optionally includes three more posts in between the commissure posts, optionally in order to support the commissure posts.

In some embodiments the downstream portion 1904, the balcony, is optionally constructed as a separate component which optionally has a mesh design, and is optionally connected via sutures/welding/other to the upstream portion 1902, the onion, in order to construct an entire cardiac valve support.

FIGS. 19C and 19D depict an example embodiment downstream portion 1904 with three commissure posts 1910 and three arches 1912.

In some embodiments the upstream portion 1902 or onion is optionally stent-like, optionally made of a metallic mesh, optionally a shape-memory mesh.

In some embodiments the downstream portion 1904 optionally includes three commissure posts 1910, and arches 1912 spanning between the commissure posts 1910.

In some embodiments the downstream portion 1904 include a distribution of struts 1914 whose tops describe a line which imitates functions of the balcony 1808 of FIGS. 18A-C. In such embodiments the struts 1914 perform a sealing function similarly to the sealing function of the balcony 1808, and/or potentially provide an anchoring mechanism, using tips of the struts 1914 to push against sides of the heart.

In some embodiments the strut 1914 design enables a thinner profile for the cardiac valve support when folded into a tube such as a catheter for delivery into a heart.

Reference is now made to FIGS. 20A, 20B and 20C, which are simplified illustrations of a cardiac valve support according to an example embodiment of the invention.

FIG. 20A is an isometric view and FIGS. 20B and 20C are side view from different angles of a cardiac valve support 2000.

FIGS. 20A, 20B and 20C depict a configuration of a cardiac valve support 2000 with an upstream portion 2004, onion, and a downstream portion 2002.

In some embodiments the upstream portion 2004 or onion is optionally stent-like, optionally made of a metallic mesh, optionally a shape-memory mesh.

In some embodiments the downstream portion 2002 optionally includes three commissure posts 2006, and arches 2008 spanning between the commissure posts 2006.

Figure 21A:
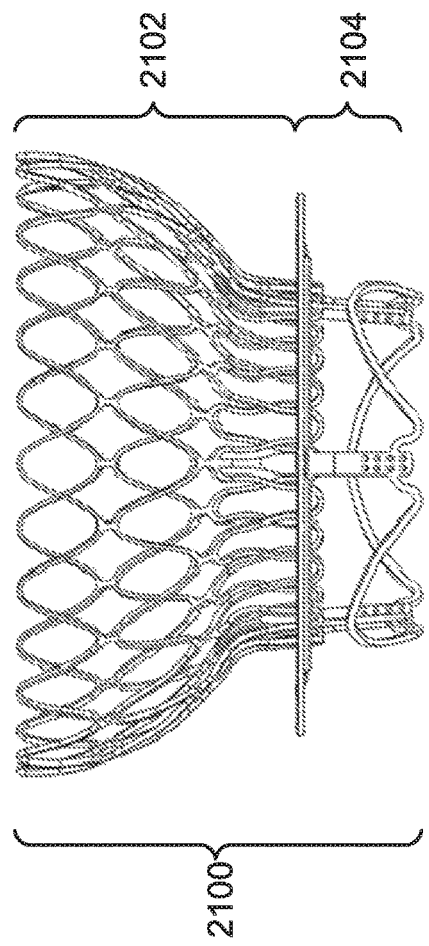
FIGS. 21A, 21B and 21C are simplified illustrations of a cardiac valve support according to an example embodiment of the invention.
Figure 21B:
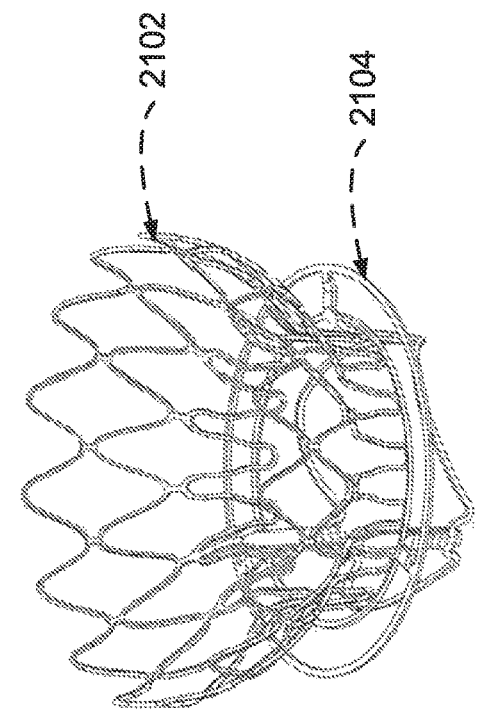
Figure 21C:
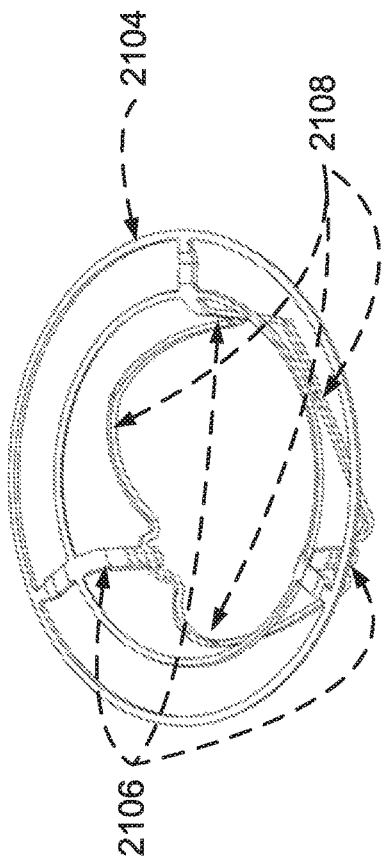

Reference is now made to FIGS. 21A, 21B and 21C, which are simplified illustrations of a cardiac valve support 2100 according to an example embodiment of the invention.

FIG. 21A is a side view and FIG. 21B is an isometric view of the cardiac valve support 2100, and FIG. 21C is an isometric view of a downstream portion 2104 of the cardiac valve support 2100.

In some embodiments an upstream portion 2102, an onion, similar to the onion embodiment depicted in FIGS. 20A-C, and a downstream portion 2104 such as the embodiment depicted in FIG. 21C to form the cardiac valve support 2100 depicted in FIGS. 21A and 21B.

The downstream portion 2104 depicted in FIGS. 21A, 21B and 21C is optionally made from a metal plate cut to a design and shape specific to the balcony, or downstream portion 2104. In some embodiments, making the balcony 2104 from a metal sheet rather than a metal tube potentially enables a more continuous contact line with surrounding sub-annular tissue for better sealing.

Reference is now made to FIGS. 22A, 22B and 22C, which are simplified illustrations of a cardiac valve support 2200 according to an example embodiment of the invention.

FIGS. 22A and 22B are side views from different angles of the cardiac valve support 2200, and FIG. 22C is an isometric view of the cardiac valve support 2100.

FIGS. 22A, 22B and 22C depict an upstream portion 2202, also termed an onion, and a downstream portion 2204, also termed a balcony. FIGS. 22A, 22B and 22C depict three commissure posts 2208 and support arcs 2206.

In some embodiments an upstream portion 2202, similar to the downstream portion 2204, are attached to each other, optionally at the commissure posts 2208, to produce the cardiac valve support 2200.

In some embodiments additional posts are added between each the commissure posts 2208 in order to strengthen the embodiment to resist the heart contractions.

In some embodiments the downstream portion 2204 and/or the upstream portion 2202 are optionally made from a metal plate cut to a design and shape specific to the balcony, or downstream portion 2204 and/or to the upstream portion 2202. In some embodiments, making the downstream and/or upstream portions from a metal sheet rather than a metal tube potentially enables a more continuous contact line with surrounding tissue for better sealing.

Figure 23:
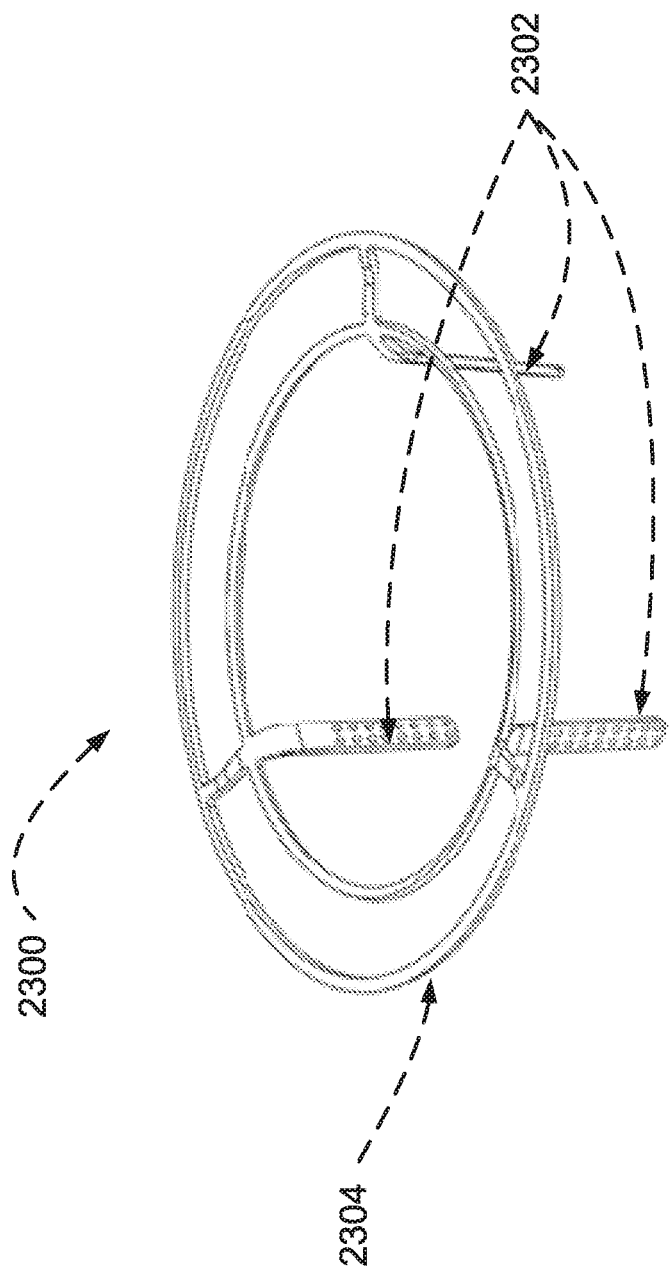
FIG. 23 is a simplified illustration of a portion of a cardiac valve support according to an example embodiment of the invention.

Reference is now made to FIG. 23, which is a simplified illustration of a portion 2300 of a cardiac valve support according to an example embodiment of the invention.

FIG. 23 depicts a portion 2300 of a cardiac valve support, which may optionally serve as a downstream portion, a balcony, or as an upstream portion, an onion.

In some embodiments two instances of the portion 2300 may optionally be combined in order to produce a cardiac valve support with one instance of the portion 2300 acting as an upstream portion, and one instance of the portion 2300 acting as a downstream portion.

In an instance of the portion 2300 which serves as the downstream portion, FIG. 23 depicts components which serve as a balcony 2304 and as commissure posts 2302.

In an instance of the portion 2300 which serves as the upstream portion, the balcony 2304 serves as an onion and the commissure posts 2302 optionally serve to attach the upstream portion to the downstream portion.

The two instances are optionally attached to each other. In some embodiments the two instances are attached to each other by attaching the commissure posts 2302 to each other.

In some embodiments the portion 2300 is optionally made from a metal plate cut to a design and shape specific to the portion 2300. In some embodiments, making the portion 2300 from a metal sheet rather than a metal tube potentially enables a more continuous contact line with surrounding cardiac tissue for potentially better sealing and/or for reducing injury to tissue by spreading forces over a larger area.

Reference is now made to FIGS. 24A, 24B and 24C, which are simplified illustrations of a cardiac valve support 2400 according to an example embodiment of the invention.

FIG. 24A is a side view of the cardiac valve support 2400, FIG. 24B is a top view of the cardiac valve support 2400, and FIG. 24C is an isometric view of the cardiac valve support 2400.

FIGS. 24A, 24B and 24C depict an upstream portion 2402, also termed an onion, and a downstream portion 2404, also termed a balcony. FIGS. 24A, 24B and 24C also depict three commissure posts 2406.

In the example embodiments depicted in FIGS. 24A, 24B and 24C the commissures posts 2406 optionally include three or more posts, and the onion 2402, the balcony 2404 and commissures support reinforcements are optionally constructed of a wire which is twisted and braided to form the above-mentioned components. In some embodiments the wire is a single wire braided to form the above-mentioned components.

It is expected that during the life of a patent maturing from this application many relevant artificial cardiac valves will be developed and the scope of the term artificial cardiac valve is intended to include all such new technologies a priori.

As used herein the term "about" refers to ±10%.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for artificial mitral valve support comprising:
   an expandable frame configured so at least part of the frame can expand larger than a natural mitral valve annulus, to prevent the frame from shifting downstream of the natural mitral valve annulus;
   a pair of commissure posts attached at one end to the frame, the commissure posts configured to extend downstream of the mitral valve annulus through the commissures of the natural mitral valve;
   a posterior extension attached at a first end to the frame, the posterior extension configured to extend downstream of the mitral valve annulus and partway back and out, pushing a posterior leaflet of the natural mitral valve toward a ventricle wall;
   a supporting arch attaching a downstream end of a first one of the commissure posts to a downstream end of the posterior extension to a downstream end of a second one of the commissure posts; and
   a pair of anterior leaflet hooks, each one of the pair of anterior leaflets hooks configured to engage chordae attached to the anterior leaflet and pull the anterior leaflet in opposing directions.

2. The device of claim 1 in which the supporting arch comprises a bend for accommodating papillary muscles.

3. The device of claim 1 and further comprising a plurality of anterior leaflet grabbers, each one of the plurality of anterior leaflet grabbers comprising one end attached to the frame and one end configured to grasp the anterior leaflet of the natural mitral valve.

4. The device of claim 1 and further comprising a pair of trigon anchors, each one of the pair of trigon anchors comprising one end attached to the frame and one end configured to push against a cardiac valve trigon.

5. The device of claim 1 in which the supporting arch is configured to be between 2 and 20 millimeters below an annular plane of the natural mitral valve when placed in a natural mitral valve.

6. The device of claim 5 in which the supporting arch is covered by a sheet of flexible material.

7. The device of claim 1 in which the frame comprises a D-shaped section of the frame configured to be placed at the natural mitral valve annulus and push the natural mitral valve annulus into a shape of the D-shaped section.

8. The device of claim 7 in which the supporting arch is configured to be between 5 and 20 millimeters larger in diameter than the D-shaped section of the frame.

9. The device of claim 7 in which the supporting arch is configured to be between 2 and 20 millimeters distant from an upstream edge of the D-shaped section of the frame.

10. The device of claim 7 in which the D-shaped section comprises a lumen having lumen walls parallel to an axis of a natural mitral valve annulus.

11. The device of claim 10 in which the lumen walls of the D-shaped section are in a range between 5 millimeters and 15 millimeters long.

12. The device of claim 1 and further comprising a commissure arch attaching a downstream end of a first one of the commissure posts to a downstream end of a second one of the commissure posts.

13. A method of supporting an artificial mitral valve comprising:
providing a frame for anchoring the artificial mitral valve, configured to be placed upstream of a natural mitral valve annulus and shaped to be able to expand to a diameter larger than the natural mitral valve annulus, to prevent the frame from shifting downstream of the natural mitral valve annulus, the frame further comprising:
a pair of commissure posts attached at one end to the frame, the commissure posts configured to extend downstream of a mitral valve annulus through the commissures of the natural mitral valve;
a posterior extension attached at a first end to the frame, the posterior extension configured to extend downstream of the mitral valve annulus and partway back and out, pushing a posterior leaflet of the natural mitral valve toward a ventricle wall; and
a supporting arch attaching a downstream end of a first one of the commissure posts to a downstream end of the posterior extension to a downstream end of a second one of the commissure posts; and
a pair of anterior leaflet hooks, each one of the pair of anterior leaflets hooks configured to engage chordae attached to the anterior leaflet and pull the anterior leaflet in opposing directions,
placing at least part of the frame in a left cardiac atrium;
passing the posterior extension and the supporting arch through the natural mitral valve commissures so as to push against the posterior leaflet of the natural mitral valve toward a ventricle wall; and
locating the commissure posts at the natural mitral valve commissures.

14. The method of claim 13, in which the frame further comprises a pair of hooks, and further comprising using each one of the pair of hooks to engage chordae attached to an anterior leaflet.

15. The method of claim 13 in which the frame further comprises anterior leaf grabbers, the anterior leaf grabbers comprising a plurality of extensions, each one of the plurality of extensions comprising one end attached to the frame and one end configured to grasp an anterior leaflet of the natural mitral valve, and further comprising using the anterior leaf grabbers to grasp the natural anterior mitral valve leaflet.

16. The method of claim 13 in which the frame comprises a D-shaped section of the frame configured to be placed at the natural mitral valve annulus and push the natural mitral valve annulus into a shape of the D-shaped section, and further comprising placing the D-shaped section of the frame at the natural mitral valve annulus.

17. A device for artificial mitral valve support comprising:
an expandable frame configured so at least part of the frame can expand larger than a natural mitral valve annulus, to prevent the frame from shifting downstream of the natural mitral valve annulus;
a pair of commissure posts attached at one end to the frame, the commissure posts configured to extend downstream of the mitral valve annulus through the commissures of the natural mitral valve;
anterior leaflet grabbers, the anterior leaflet grabbers comprising a plurality of extensions, each one of plurality of extensions comprising one end attached to the frame and one end configured to grasp an anterior leaflet of the natural mitral valve; and
a pair of hooks, each one of the pair of hooks configured to engage chordae attached to the anterior leaflet and pull the anterior leaflet in opposing directions.

18. The device of claim 17 and further comprising:
a posterior extension attached at a first end to the frame, the posterior extension configured to extend downstream of the mitral valve annulus and partway back and out, pushing a posterior leaflet of the natural mitral valve toward a ventricle wall; and
a supporting arch attaching a downstream end of a first one of the commissure posts to a downstream end of the posterior extension to a downstream end of a second one of the commissure posts.

* * * * *